United States Patent
Dolnik et al.

(10) Patent No.: US 11,478,125 B2
(45) Date of Patent: Oct. 25, 2022

(54) SYSTEMS AND METHODS FOR ASSESSMENT AND MONITORING OF A MUCOSAL DISEASE IN A SUBJECTS GASTROINTESTINAL TRACT

(71) Applicant: GIVEN IMAGING LTD., Yoqneam (IL)

(72) Inventors: Inessa Dolnik, Haifa (IL); Orit Elkayam, Givat Ela (IL); Assaf Stein, Kadima (IL); Alon Lapidus, Lehavim (IL)

(73) Assignee: GIVEN IMAGING LTD., Yoqneam (IL)

(*) Notice: Subject to any disclaimer, the term of this patent is extended or adjusted under 35 U.S.C. 154(b) by 971 days.

(21) Appl. No.: 16/314,021

(22) PCT Filed: Jun. 29, 2017

(86) PCT No.: PCT/IL2017/050728
§ 371 (c)(1),
(2) Date: Dec. 28, 2018

(87) PCT Pub. No.: WO2018/002935
PCT Pub. Date: Jan. 4, 2018

(65) Prior Publication Data
US 2019/0244351 A1 Aug. 8, 2019

Related U.S. Application Data

(60) Provisional application No. 62/491,486, filed on Apr. 28, 2017, provisional application No. 62/357,088, filed on Jun. 30, 2016.

(51) Int. Cl.
*A61B 1/04* (2006.01)
*G06T 7/00* (2017.01)
(Continued)

(52) U.S. Cl.
CPC .... *A61B 1/000094* (2022.02); *A61B 1/00009* (2013.01); *A61B 1/041* (2013.01);
(Continued)

(58) Field of Classification Search
CPC .............. G06T 7/0012; G06T 7/11; G06T 2207/10068; G06T 2207/30028;
(Continued)

(56) References Cited

U.S. PATENT DOCUMENTS

| | | | |
|---|---|---|---|
| 8,682,142 B1 | 3/2014 | Boskovitz et al. | 386/278 |
| 8,768,024 B1 | 7/2014 | Zingman et al. | 382/128 |

(Continued)

FOREIGN PATENT DOCUMENTS

| | | | | |
|---|---|---|---|---|
| JP | 2012249936 A | 12/2012 | | A61B 1/04 |
| WO | WO 2015/052351 A1 | 4/2015 | | G06T 7/00 |

OTHER PUBLICATIONS

Japanese Office Action issued in corresponding application JP 2018-568969 dated May 11, 2021, together with English language translation (12 pages).

(Continued)

*Primary Examiner* — Andrew W Johns
(74) *Attorney, Agent, or Firm* — Carter, DeLuca & Farrell LLP

(57) ABSTRACT

A computerized-method for a mucosal assessment of a mucosal disease in a Gastrointestinal Tract (GIT) of a subject, including receiving a stream of images of at least a portion of the GIT, parsing the stream into a plurality of segments, wherein each segment corresponds to a region of the at least portion of the GIT, obtaining a set of values for each segment, wherein the set of values refers to the pathological involvement of the segment in the mucosal disease and to severity of mucosal manifestation of the mucosal disease in the segment, and based on said set of (Continued)

values for each segment, generating a representation indicating the location and severity of the mucosal manifestation of the mucosal disease in the entirety of the at least portion of the subject's GIT, thereby allowing to assess the condition of the mucosal disease in the at least portion of the GIT.

18 Claims, 22 Drawing Sheets

(51) Int. Cl.
    *A61B 1/00*     (2006.01)
    *A61B 5/00*     (2006.01)
    *G06T 7/11*     (2017.01)
    *G16H 10/60*     (2018.01)
    *G16H 30/40*     (2018.01)

(52) U.S. Cl.
    CPC .............. *A61B 5/42* (2013.01); *G06T 7/0012* (2013.01); *G06T 7/11* (2017.01); *G16H 10/60* (2018.01); *G16H 30/40* (2018.01); *G06T 2207/10016* (2013.01); *G06T 2207/10068* (2013.01); *G06T 2207/30028* (2013.01); *G06T 2207/30092* (2013.01)

(58) Field of Classification Search
    CPC .......... G06T 2207/30092; G16H 30/40; G16H 50/20; A61B 1/00009; A61B 1/000094; A61B 1/041; A61B 1/273; A61B 1/2733; A61B 1/2736; A61B 1/31; A61B 5/42; A61B 5/4216; A61B 5/4222; A61B 5/4238; A61B 5/4255
    See application file for complete search history.

(56) References Cited

U.S. PATENT DOCUMENTS

| | | | |
|---|---|---|---|
| 2001/0041964 A1 | 11/2001 | Grass et al. | 702/19 |
| 2007/0224191 A1 | 9/2007 | Walters et al. | 424/133.1 |
| 2008/0039692 A1 | 2/2008 | Hirakawa | 600/160 |
| 2008/0162352 A1 | 7/2008 | Gizewski | 705/50 |
| 2010/0042084 A1 | 2/2010 | Nariyuki et al. | 606/15 |
| 2014/0334698 A1* | 11/2014 | Tanaka et al. | A61B 1/0005 382/128 |
| 2015/0011542 A1 | 1/2015 | Boelsterli | A61K 31/5377 |
| 2019/0304093 A1* | 10/2019 | Duval et al. | A61B 5/746 |

OTHER PUBLICATIONS

Iakovidis et al., "Software for enhanced video capsule endoscopy: challenges for essential progress", Nature Reviews Gastroenterology & Hepatology, Mar. 2015, pp. 172-186, vol. 12.
Lewis et al., "Evaluation of Capsule Endoscopic Images", Video Capsule Endoscopy: A Reference Guide and Atlas, 2015, pp. 31-47.
Examiner's Decision of Rejection issued in corresponding Japanese Application No. 2018-568969 dated Sep. 7, 2021, together with English language translation (5 pages).

* cited by examiner

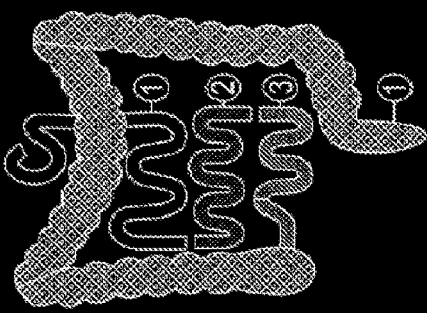
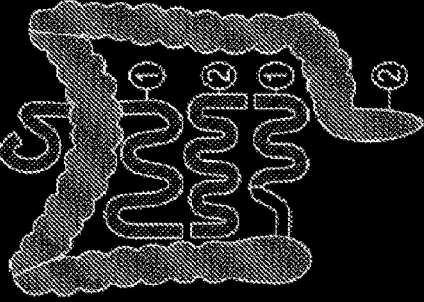
FIG. 18

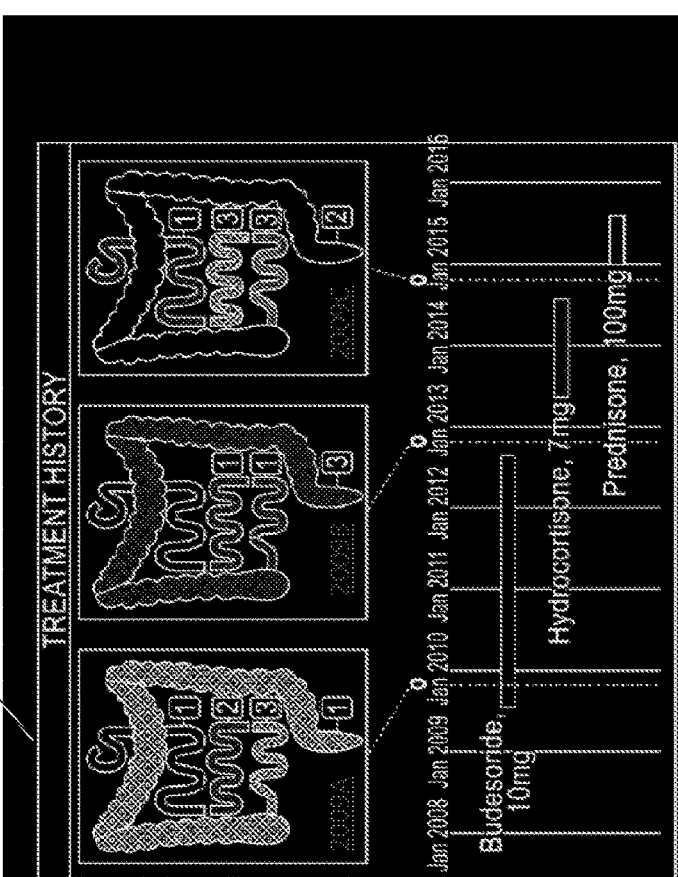
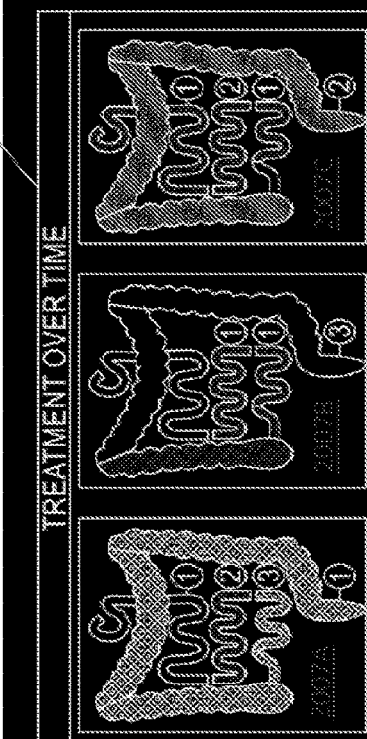
FIG. 20A
FIG. 20B

SYSTEMS AND METHODS FOR ASSESSMENT AND MONITORING OF A MUCOSAL DISEASE IN A SUBJECTS GASTROINTESTINAL TRACT

CROSS-REFERENCE TO RELATED APPLICATIONS

This application is a National Phase Application of PCT International Application No. PCT/IL2017/050728, International Filing Date Jun. 29, 2017, claiming priority of US Patent Application(s) No(s). 62/357,088, filed Jun. 30, 2016, and U.S. Patent Application No. 62/491,486, filed Apr. 28, 2017, each of which are hereby incorporated by reference.

FIELD OF THE INVENTION

The present invention relates to a method and system for standardized assessment and/or monitoring of a mucosal disease in the Gastrointestinal Tract ("GIT") of a subject. More specifically, but not limited to, the present invention relates to systems and methods for assessing and/or monitoring of a mucosal disease in a standardized manner by characterizing, scoring, summarizing and/or displaying images of regions of a subject's GIT based on images captured during one or more procedures.

BACKGROUND OF THE INVENTION

The GIT, referring to the alimentary tract extending from the mouth until the anus, is one of the largest organs in the body, serving a number of functions centered on consumption, digestion and absorption of nutritional products and water; and excretion of waste products. This alongside the important immunological defense against the concomitant exposure to foreign substances, making it the largest immune organ in the body. The GIT is divided along its length into various discrete regions, both in terms of structure and in terms of function. However, there are basic uniform similarities that are maintained throughout the length of the GIT, particular in terms of the tissue organization along the intestinal tube.

The innermost layer of tissue in the GIT is the mucosa. This layer is very important as it comes in direct contact with the luminal contents of the GIT, and is therefore exposed to mechanical, chemical and infectious stress. The mucosa is histologically composed of, from the lumen outwards, the epithelium, the lamina propria and the muscularis mucosa. The mucosal epithelium is central to digestion and absorption of nutritional products, accomplished by enteroendocrine cells and enterocytes. However, the exact cellular structure of the epithelium, e.g. villi projections and crypts, varies greatly depending on the specific function of each GIT region. The lamina propria is composed predominantly of connective tissue and beneath it is the thin muscular layer of the muscularis mucosa. This muscular layer gives the mucosa the macroscopic appearance of folds and ridges.

As the mucosa is the viewing pane through which the GIT can be examined endoscopically, this layer and the alterations in its region-specific normal appearance, are indicative of underlying pathological processes. There are many disease states that are manifest with mucosal pathology, which may present as: loss of macroscopic normal structures (e.g. villi), erosions and ulcerations, vascular malformations, metaplasia and/or neoplasia. These can be the result of, but not limited to, inflammatory bowel diseases (IBD), vascular diseases, autoimmune diseases, malabsorption diseases, graft-versus-host diseases, drug-induced disease, radiation-induced diseases and malignancy. Due to the ability to directly observer these mucosal diseases endoscopically, there is a unique opportunity and capability to assess disease progression and responsiveness to therapy.

One of the classic examples of a systemic disease which has significant mucosal manifestations is IBD. Crohn's disease (CD) and ulcerative colitis (UC), two major forms of IBD, can be characterized by a tendency for chronic and/or relapsing immune activation and inflammation of a subject's GIT, mainly the small bowel (SB) and the colon, respectively. Typical points of interest in IBD, and specifically in CD patient management, have been achievement of periods of symptomatic remission and/or monitoring for development of complications. To this end, the former are evaluated through indices of daily activity and quality of life (e.g., Crohn's Disease Activity Index (CDAI), Inflammatory Bowel Disease Questionnaire (IBDQ), etc.) and laboratory evaluation; the latter, are evaluated via modalities that allow for specific detection of the complications, both extra-intestinal (e.g., fistula, abscess and stricture, via magnetic resonance enterography or computed tomography enterography (MRE or CTE)) and intestinal (e.g., colonic dysplasia and carcinoma, via tissue biopsies).

Recently there has been a departure from a solely symptomatic approach to CD patient management. The points of interest are now being focused on mucosal disease assessment and detection of mucosal healing, i.e. returning the diseased mucosa back to healthy and normally appearing tissue. This is central to preservation of gut function and alteration of the natural history of the disease. Contrary to past conceptions, there is not always a linear correlation between a patient's clinical presentation and his mucosal disease involvement.

Thus, in addition to evaluating the clinical, laboratory and wellbeing state of a subject (e.g., patient), physicians are interested in estimating the mucosal inflammatory activity of the intestinal disease and assess it over the course of time. It is paramount to include endoscopic assessment of the mucosal disease in order to obtain a comprehensive portrayal of the patient's disease and effectively manage the patient's therapy, aid in clinical decision making, and hence improve the patient's outcome and thwart progression to structural complications. Thus, mucosal assessment is an important part of treatment planning, and mucosal monitoring can be an important end point in clinical trials and a desirable goal in clinical practice.

To aid in clinical decision making when treating mucosal disease patients, a variety of techniques to estimate disease activity and/or mucosal manifestations can be used. These techniques include radiological methods (CTE and MRE) and/or endoscopic methods (conventional and capsule endoscopy); and, biomarkers of inflammation and mucosal permeability (e.g. calprotectin and c-reactive protein (CRP)).

Radiological modalities do not directly show mucosal inflammation but rather show trans-mural changes and clues to significant mucosal inflammatory processes. As such, these modalities do not directly show the extent nor the actual pathologies manifest in the mucosa, and are usually associated with undesirable radiation. MRE, a radiation-free procedure, is an effective method for trans-mural assessment of mucosal diseases, but it can be expensive and as a result is not widely available. Both CTE and MRE have been shown to be inferior compared to capsule endoscopy in assessment of proximal (proximal to terminal ileum) small bowel mucosal disease. Correlation between inflammatory markers and endoscopic findings exists, but while these methods can be easy and inexpensive, they cannot arrive at a comprehensive assessment of mucosal disease severity. This is because, for example, mucosal disease extent and location cannot be assessed by such methods. In addition, it has been shown that inflammatory markers have a high false negative (FN) rate, resulting in low sensitivity for mild disease.

In the process of evaluating endoscopy procedures (e.g. wireless capsule endoscopy video), physicians typically look for particular images that demonstrate the mucosal manifestation of the mucosal disease. On the one hand, only considering a few particular images during assessment can result in a limited and possible inaccurate or even detrimental assessment of the disease. On the other hand, reviewing the entire video before reaching an assessment, requires that the physician remember what was seen in each segment or region, and "carry" this information with him throughout the video review. This can require the physician to spend an extensive amount of time (over 90 minutes) viewing a video and either taking notes, or remembering what is being viewed. This of course can also lead to inaccurate assessment of the disease.

Various diseases scoring algorithms have been developed and validated for these aforementioned modalities. However, to date, there is not a wide agreement regarding a gold standard that should be used to monitor mucosal involvement throughout the GIT, nor is there agreement regarding indices for mucosal healing, disease activity and/or response to treatment. Some of the mucosal diseases, such as CD, typically distribute over the SB and the colon while known procedures are usually only each individually specific for either the SB, the colon or the colon with a very short part of SB.

Therefore, it can be desirable to provide methods and systems for mucosal assessment and monitoring of mucosal diseases of the GIT, that are sensitive, specific, consistent and therefore comparative, inexpensive, widely available, easy to use and/or noninvasive.

SUMMARY

There is provided in accordance with the present disclosure, a computerized-method for a mucosal assessment of a mucosal disease in a Gastrointestinal Tract (GIT) of a subject, the method comprising: receiving a stream of images of at least a portion of the subject's GIT; parsing the stream of images into a plurality of segments, wherein each segment corresponds to a region of the at least portion of the subject's GIT; obtaining a set of values for each of said segments, wherein the set of values refers to the pathological involvement of the segment in the mucosal disease and to severity of mucosal manifestation of the mucosal disease in the segment; and based on said set of values for each segment, generating a representation indicating the location and severity of the mucosal manifestation of the mucosal disease in the entirety of the at least portion of the subject's GIT, thereby allowing to assess the condition of the mucosal disease in the at least portion of the subject's GIT.

There is further provided in accordance with the present disclosure, a computerized-method for a mucosal assessment of a mucosal disease in a Gastrointestinal Tract (GIT) of a subject, the method comprising: receiving a stream of images of at least a portion of the subject's GIT; parsing the stream of images into a plurality of segments, wherein each segment corresponds to a region of the at least portion of the subject's GIT, and wherein the GIT regions are of a substantially (e.g. +−5% or +−10%) equal length; receiving a set of values for each of said segments from a user, wherein the set of values refers to the pathological involvement of the segment in the mucosal disease and to severity of mucosal manifestation of the mucosal disease in the segment; and based on said set of values for each segment, generating a representation indicating the location and severity of the mucosal manifestation of the mucosal disease in the entirety of the at least portion of the subject's GIT, thereby allowing to assess the condition of the mucosal disease in the at least portion of the subject's GIT.

There is further provided in accordance with the present disclosure, a system for a mucosal assessment of a mucosal disease in a Gastrointestinal Tract (GIT) of a subject, the system comprising: a storage device having stored thereon instructions for: receiving a stream of images of at least a portion of the subject's GIT; parsing the stream of images into a plurality of segments, wherein each segment corresponds to a region of the at least portion of the subject's GIT; obtaining a set of values for each of said segments, wherein the set of values refers to the pathological involvement of the segment in the mucosal disease and to severity of mucosal manifestation of the mucosal disease in the segment; and based on said set of values for each segment, generating a representation indicating the location and severity of the mucosal manifestation of the mucosal disease in the entirety of the at least portion of the subject's GIT; at least one hardware processor configured to execute said instructions; and a display configured to display the generated representation.

In another aspect of the present disclosure, said computerized-method further comprises displaying to a user said stream of images while indicating said segments or GIT regions in said displayed stream of images; and directing said user to input one or more values of said set of values for each of said segments, wherein the GIT regions are of a substantially equal length.

In another aspect of the present disclosure, the directing of said user to input said one or more values for each of said segments is performed during or immediately after its display and prior to the display of the next segment.

In another aspect of the present disclosure, the at least portion of the GIT comprises the small bowel and the colon.

In another aspect of the present disclosure, the stream of images is parsed into four segments corresponding to three regions of the small bowel and the colon.

In another aspect of the present disclosure, the set of values obtained for each segment comprises: a value indicating the highest degree of severity of the mucosal manifestation in the segment, a value indicating the common degree of severity of the mucosal manifestation in the segment, and a value indicating the extent of the mucosal manifestation in the segment.

In another aspect of the present disclosure, the extent value of a mucosal manifestation indicates the portion of the tissue surface of the respective GI region displaying mucosal manifestation.

In another aspect of the present disclosure, the stream of images is captured by a capsule endoscope and the at least portion of the stream of images is parsed into a plurality of segments via a computerized assessment of the capsule endoscope's progress through the subject's GIT.

In another aspect of the present disclosure, the representation comprises an anatomical graphical representation of the at least portion of the GIT depicting each of its GIT regions and one or more values of the obtained set of values for each of said GIT regions.

In another aspect of the present disclosure, the obtaining of the set of values for each of said segments comprises identifying mucosal manifestation of the mucosal disease in said each of said segments.

In another aspect of the present disclosure, the obtaining of the set of values for each of said segments comprises calculating one or more values of the set of values for each of said segments.

In another aspect of the present disclosure, set of values further refer to the pathological involvement of one or more portions of interest of the GIT.

In another aspect of the present disclosure, a computerized-method for monitoring a mucosal disease in a subject's GastroIntestinal Tract (GIT) comprising: obtaining a plurality of representations indicating the location and severity of mucosal manifestation of the mucosal disease in at least a portion of the subject's GIT, wherein each representation of the plurality of representations is generated according to said computerized-method, and wherein each representation of the plurality of representations is based on a stream of images captured in the subject's GIT during a procedure having a unique date; and displaying the plurality of representations of the at least portion of the subject's GIT in an adjacent manner; and tagging each representation with its corresponding unique date, thereby allowing a user to monitor the condition of the mucosal disease through time.

In another aspect of the present disclosure, each representation comprises an anatomical graphical representation of the at least portion of the GIT depicting each of its GIT regions and one or more values of the obtained set of values for each of said GIT regions, and the anatomical graphical representations are displayed along a timeline according to their corresponding unique dates.

In another aspect of the present disclosure, said computerized-method further comprises receiving medical treatment history data for the subject comprising a treatment start and stop data; displaying the plurality of representations along a timeline according to their corresponding unique dates; and displaying along the timeline at least a portion of the medical treatment history data.

In another aspect of the present disclosure, the medical treatment history data comprises medication prescribed to the subject.

In another aspect of the present disclosure, the GIT regions are of a substantially equal length.

Any of the above aspects and embodiments of the present disclosure may be combined without departing from the scope of the present disclosure.

BRIEF DESCRIPTION OF THE DRAWINGS

The principles and operation of the system and method according to the present invention can be better understood with reference to the drawings, and the following description, it being understood that these drawings are given for illustrative purposes only and are not meant to be limiting, wherein:

FIG. 3 is an exemplary screen shot of a start-up screen for a system for mucosal assessment and monitoring of a mucosal disease in a GIT of a subject, according to an illustrative embodiment of the invention.

FIG. 4 is an exemplary screen shot of an exemplary list of findings files that can be presented to a user for any available video, according to an illustrative embodiment of the invention.

FIG. 18 is an exemplary screen shot of comparison between two assessment reports for two procedures performed on two different dates for the same patient, according to an illustrative embodiment of the invention.

FIG. 20A and FIG. 20B are exemplary reports, each including multiple anatomical graphical representations and corresponding medical treatment along a timeline, according to an illustrative embodiment of the invention.

Figure 1:
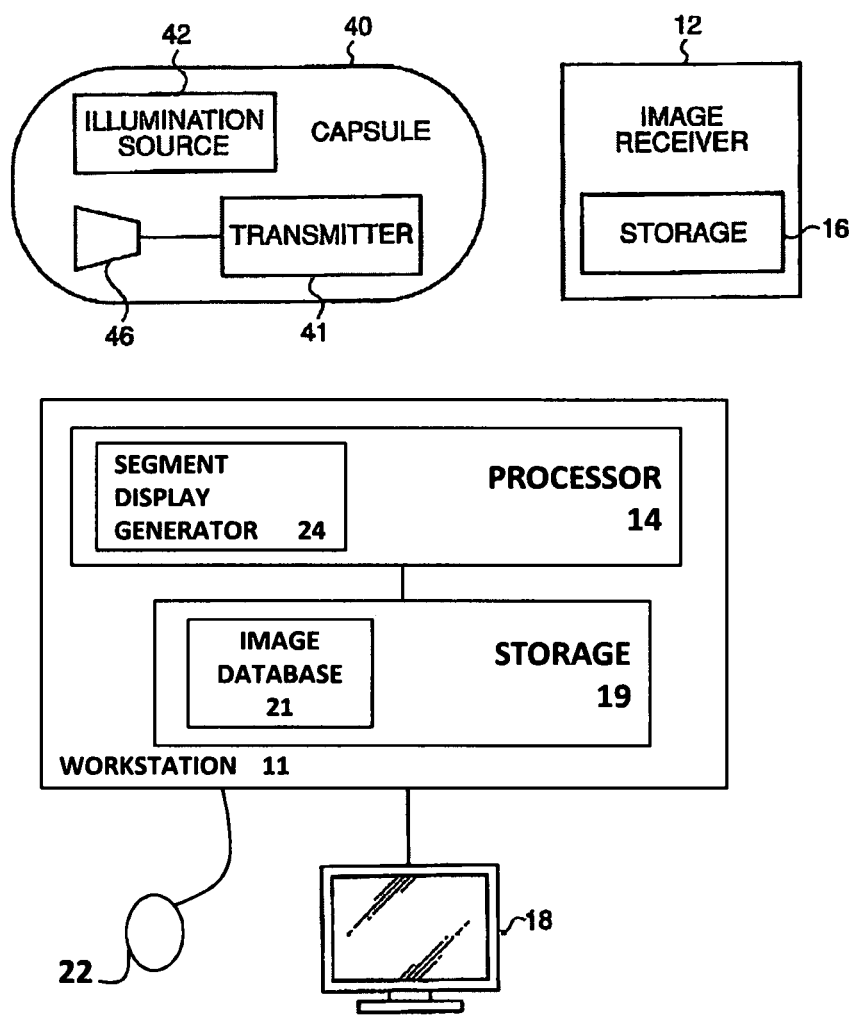
FIG. 1 is a schematic diagram of a Capsule Endoscopy (CE) imaging system, according to an illustrative embodiment of the invention.

It will be appreciated that for simplicity and clarity of illustration, elements shown in the figures have not necessarily been drawn to scale. For example, the dimensions and/or aspect ratio of some of the elements can be exaggerated relative to other elements for clarity. Further, where considered appropriate, reference numerals can be repeated among the figures to indicate corresponding or analogous elements throughout the serial views.

DETAILED DESCRIPTION OF THE INVENTION

According to some embodiments, assessment of mucosal manifestations of a mucosal disease in a gastrointestinal track of a subject (e.g., patient) can be performed.

A stream of images of the subject's GIT can be received. The stream of images can be captured by procedures which image or at least indicate characteristics referring to one or more mucosal manifestations of disease within the GIT, such as capsule endoscopy, colonoscopy or gastroscopy. The stream of images can be parsed into a plurality of segments, each segment can show a region of the subject's GIT. In some embodiments, the regions can be of substantially equal length.

A set of values that refer to and/or are indicative of, at least, the pathological involvement and disease severity of the segment with respect to the mucosal manifestation of the disease are assigned to each segment and its corresponding GIT region. The set of values can include, for example, a most typical or common mucosal manifestation value, a most severe mucosal manifestation value and an extent value. Thus, if the assessed mucosal manifestation includes lesions, the set of values can include a most typical or common lesion value, a most severe lesion value and an extent value. Severity related values indicative of the presence/non-presence of mucosal manifestation in a GIT region can also indicate that the GIT region is involved/uninvolved in the disease correspondingly. For example, a most severe mucosal manifestation value which equals zero assigned to a GIT region, can indicate that the GIT region is not involved in the disease and vice versa. A most severe mucosal manifestation value which is different than zero assigned to a GIT region, can indicate that the GIT region is involved in the disease.

All of the values or only a portion of them may be received by a user. Alternatively or additionally, all of the values or a portion of them may be automatically calculated by the disclosed systems and methods. In some embodiments, each of one or more of the values may be determined based on a combination of both, i.e., automatic calculation and manual identification and/or assessment performed by a user.

The values for each segment can be displayed. The stream of images for a subject can be captured at multiple times (e.g., at different dates). For each time, an anatomical representation of the subject's GIT can be generated and displayed. The anatomical representation may indicate the different GIT regions. The anatomical representation may also present the set of values for each GIT region. Thus, the anatomical representation can be indicative of the severity of the mucosal manifestation of the disease in the entire portion of the GIT (or the entire GIT) and of the location (may be also referred to as distribution or spread) of the mucosal manifestation within the entire portion of the GIT by the different GIT regions. It should be indicated that the location of the mucosal manifestation may also project on its severity or prognosis, e.g. proximal SB CD having an inferior prognosis compared to only distal SB CD. In this manner, an anatomical representation of the mucosal condition of the subject's GIT can be viewed over a period of time.

The disclosed systems and methods can provide standardization of evaluation of the mucosal manifestations of a mucosal disease in a GIT of a subject, qualitative appraisal of mucosal disease involvement, and calibration of pathological points of interest within the GIT to large scale assessment of mucosal disease dynamics over time. Standardization of evaluation of the mucosal disease can allow for comparative review and management of patients over time, thus improving the overall quality of mucosal disease treatment and patient management.

The disclosed systems and methods can be highly beneficial in assessing and/or monitoring mucosal diseases having a mucosal manifestation which is non-focal (e.g. inflammatory, mal-absorptive, auto-immune, etc.). The disclosed systems and methods can be also highly beneficial in assessing and monitoring mucosal diseases that the severity and/or location of their mucosal manifestation within the GIT can alter over time.

The subject can be any mammal having a GIT. The subject can be a human patient. In the foregoing description, subject and patient are used interchangeably, but the use of subject is not meant to be limiting to a human patient.

Unless stated otherwise, all of the operations described herein, including identifying landmarks or providing one or more values, can be performed manually, by a user, or automatically, e.g., by one or more processing units, as will be detailed herein below.

The term "gastrointestinal tract" ("GIT"), as referred to herein, may relate to the entire digestive system, extending from the mouth to the anus and includes the pharynx, esophagus, stomach and intestines, or any portion of it.

The term "GIT portion" may refer to any portion of the GIT (anatomically distinct or not) or to the entire GIT, according to the context.

The term "mucosal manifestation" as referred to herein, may relate to a macroscopic presentation of a pathological process in the mucosa such as: loss of macroscopic normal structures (e.g. loss of villi, stricture), erosions and ulcerations, vascular malformations, metaplasia and/or neoplasia, etc.

The term "mucosal disease", as referred to herein, may relate to any disease of the GIT or a portion of it that may be characterized by a mucosal manifestation. Such diseases may include, for example, inflammatory diseases (e.g. IBD), auto-immune diseases (e.g. celiac disease), vascular diseases, malabsorption diseases, graft-versus-host diseases, drug-induced diseases, radiation-induced diseases, malignancy etc.

The term "image" or "images", as referred to herein, may relate to an image, multiple images or a stream of images captured by, for example, capsule endoscopy, endoscopy (e.g., colonoscopy, gastroscopy) and/or any other suitable imaging modality as known in the art.

Reference is made to FIG. 1, which illustrates a schematic diagram of a CE imaging system according to an illustrative embodiment of the invention. In an exemplary embodiment, the system includes a capsule 40 having one or more imagers 46, for capturing images, one or more illumination sources 42, for illuminating the body lumen, and a transmitter 41, for transmitting image and possibly other information to a receiving device.

The image capture device can correspond to embodiments described in U.S. Pat. No. 7,009,634 to Iddan et al., and/or in U.S. patent application Ser. No. 11/603,123 to Gilad, but in alternate embodiments can be other sorts of image capture devices. The images captured by the imager system can be of any suitable shape including for example circular, square, rectangular, octagonal, hexagonal, etc.

Typically, located outside the subject's body in one or more locations are an image receiver 12, typically including an antenna or antenna array, an image receiver storage unit 16, a data processor 14, a data processor storage unit 19, and an image monitor or visual display unit 18, for displaying, inter alia, images recorded by the capsule 40. Data processor storage unit 19 can include an image database 21.

Typically, data processor 14, data processor storage unit 19 (e.g., a memory) and monitor 18 are part of a personal computer or workstation 11, which includes standard components such as processor 14, a memory, a disk drive, and input-output devices 22 such as a mouse and keyboard, although alternate configurations are possible. Data processor 14 can include any standard data processor, such as a microprocessor, multiprocessor, accelerator board, or any other serial or parallel high performance data processor. Data processor 14, as part of its functionality, can act as a controller controlling the display of the images (e.g., which images, the location of the images among various windows, the timing or duration of display of images, etc.).

Image monitor 18 can be a conventional video display or any other device capable of displaying image or other data. The image monitor 18 presents image data, for example, one or more GIT images, one or more anatomical graphical representations of the images captured, images in the form of still and moving pictures, motility data and/or other information.

In some embodiments, the various categories of information are displayed in windows. A window can be for example a section or area (possibly delineated or bordered) on a display or monitor; other windows can be used. Multiple monitors can be used to display images, motility properties, motility events and other data, for example, an image monitor can also be included in image receiver 12. When used in the context of a sequence of frames, a window of a set or sequence (e.g., ordered by time of capture or receipt, or another ordering) of frames can be a sequential subset of image frames within a stream of image frames.

In operation, imager 46 captures images and can send data representing the images to transmitter 41. Transmitter 41 transmits images to image receiver 12 (e.g., as frames) using, for example, electromagnetic radio waves. Image receiver 12 transfers the image data to image receiver storage unit 16. After a certain period of time of data collection, the image data stored in storage unit 16 can be transferred to the data processor 14 or the data processor storage unit 19. For example, the image receiver 12 or image receiver storage unit 16 can be taken off the patient's body and connected to a personal computer or workstation which includes the data processor 14 and data processor storage unit 19 via a standard data link, e g, a serial, parallel, USB, or wireless interface of known construction. The image data is then transferred from the image receiver storage unit 16 to an image database 21 within data processor storage unit 19.

Typically, the image stream is stored as a series of images in the image database 21, which can be implemented in a variety of known manners. Data processor 14 can analyze the data and provide the analyzed data to the image monitor 18, where a user views the image data. For example, data processor 14, or another data processor (e.g. in receiver 12) can process images and present anatomical representations of GIT of a subject. Data processor 14 operates software that, in conjunction with basic operating software such as an operating system and device drivers, controls the operation of data processor 14. The software controlling data processor 14 includes code implemented using various development platforms such as Microsoft's .NET platform, and can be implemented in a variety of known methods.

The image data recorded and transmitted by the capsule 40 can be digital color image data, although in alternate embodiments other image formats can be used. In an exemplary embodiment, each frame of image data includes 320 rows of 320 pixels each (e.g., 320 rows and 320 columns), each pixel including bytes for color and brightness, according to known methods. For example, each imager pixel can include a color sensor which can correspond to a single primary color, such as red, green, or blue. The brightness of the overall pixel can be recorded by a one byte (i.e., 0-255) brightness value. Images can be stored, for example sequentially, in data processor storage unit 19. The stored data is comprised of one or more pixel values, including color and brightness. Other image formats can be used.

Data processor storage unit 19 can store a series of images recorded by a capsule 40. The images that capsule 40 records, for example, as it moves through a patient's GIT, can be combined consecutively to form a series of images displayable as an image stream. When viewing the image stream, the user is typically presented with one or more windows on monitor 18. In alternate embodiments, multiple windows need not be used and only the image stream can be displayed. In an embodiment where multiple windows are provided, for example, an image window can provide the image stream, or still portions of that image. Another window can include buttons or other controls that can alter the display of the image, for example, stop, play, pause, capture image, step, fast-forward, rewind, or other controls. Such controls can be activated by, for example, a pointing device such as a mouse or a finger on a touch screen. The image stream can be frozen to view one frame, speeded up, or reversed; sections can be skipped; or any other method for viewing an image can be applied to the image stream.

Data processor 14 can include, or can be operationally connected, directly or indirectly, to a segment display generator 24. Segment display generator 24 can process images from the captured set of images into segments. A segmented presentation can be then generated and displayed in a predetermined section of the graphical user interface (GUI). In some embodiments, segment display generator 24 can produce a segment display, e.g. a segment color bar or other graphical presentation.

In one example, a subset of images used for generating a time bar can include images captured between certain anatomical landmarks which can be identified in the image stream. For example, between the $1^{st}$ Duodenal Image and the $1^{st}$ Cecal Image, and between the $1^{st}$ Cecal Image and the Last Rectal Image.

Two anatomical landmarks can be selected (e.g. can be predetermined in the system and/or selected by a user) and all images captured during the time the capsule traveled from a selected anatomical landmark which was captured first to the selected anatomical landmark which was captured later, can be included in the generation of a time bar.

In another example, images can be selected (e.g., by a user (e.g., a doctor) or by a computer) according to color parameters, image quality parameters, number of detected pathology candidates in the image, etc. The time bar can be generated for selected organs (esophagus, small bowel, colon, stomach, etc.), a selected GIT region or for a specified time length selected from the complete imaging procedure. In yet another example, images can be merged or fused, e.g.

based on similarity between adjacent images, and a time bar can be generated based on the subset of fused or merged images. Other image selection methods can be used for determining or selecting the subset of images, as known in the art. Different image selection methods can be combined for producing the subset of images which can be used in the generation of a time bar.

Devices according to embodiments of the present invention, including imaging, receiving, processing, storage and/or display units suitable for use with embodiments of the present invention, can be similar to embodiments described in US Patent Application Publication Number 2006/0074275, entitled "System and Method for Editing an Image Stream Captured In-Vivo", U.S. Pat. No. 7,009,634 to Iddan et al., entitled "Device for In-Vivo Imaging", and/or US Patent Application Publication Number 2007/0118012, entitled "Method of Assembling an In-Vivo Imaging Device", each assigned to the common assignee of the present application. Methods for analyzing motility within a GIT based on comparison between images captured by an in vivo imaging capsule are disclosed, for example, in U.S. Pat. No. 6,944,316 to Glukhovsky et al.

Figure 2A:
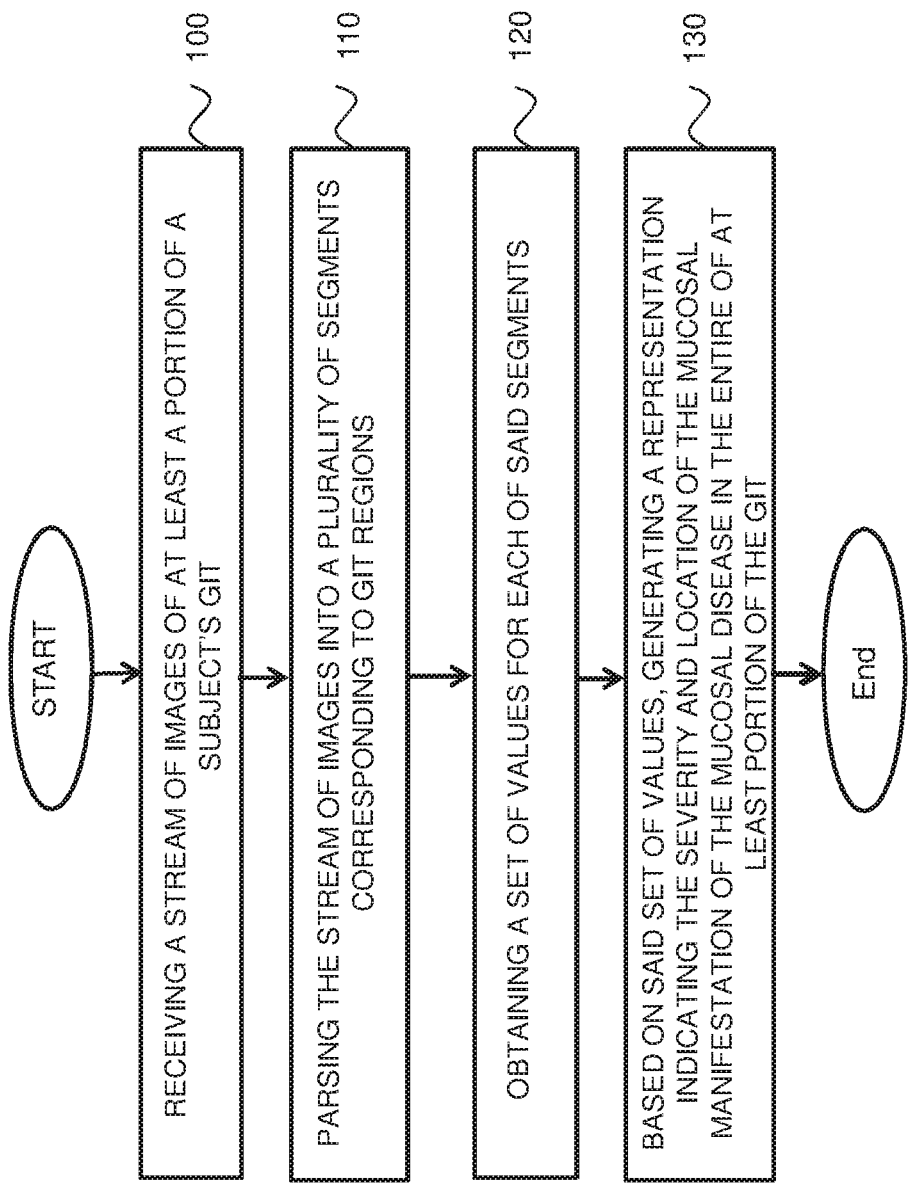
FIG. 2A is a flow chart for a method of mucosal assessment of a mucosal disease in a GIT of a subject, according to an illustrative embodiment of the invention.

FIG. 2A is a flow chart for a method of assessment of a condition of a mucosal disease in a GIT of a subject, according to an illustrative embodiment of the invention. In a step 100, a stream of images of at least a portion of the subject's GIT can be received. For example, the stream of images can be captured and therefore received from a capsule endoscope, as described above in FIG. 1. In some embodiments, where the aim is to assess the condition of an inflammatory bowel disease (e.g., Crohn's disease) a stream of images of a portion of the GIT which includes the small bowel and the colon can be obtained. In some embodiments, a subject identifier (e.g., a patient identifier), a date that the stream of images was captured, a patient diagnoses and any related medical data or any combination thereof, is further received for the obtained stream of images.

In a step 110, the stream of images can be parsed into a plurality of segments. Each segment can correspond to a region of the imaged portion of the subject's GIT. In some embodiments, the regions can be of a substantially equal length. One or more of the regions can be defined by anatomical regions, such as the small bowel or the colon. Each segment can include a varying number of image frames. In some embodiments, each of the plurality of segments is assigned an identifier such that a position of a particular segment relative to the other segments can be determined. For example, in some embodiments, the plurality of segments are sequentially labeled. In some embodiments, the identifier includes a start time and a stop time for each segment. The parsing may be performed via a computerized assessment performed by a computerized system such as workstation 11 of FIG. 1, e.g., based on a computerized assessment of the capsule endoscope's progress through the subject's GIT.

For example, a stream of images captured by a capsule endoscope, such as capsule endoscope 40 of FIG. 1, while travelling through the small bowel and the colon of a subject, may be received. The stream of images may be then parsed into four segments corresponding to three regions of the small bowel (will be also referred herein below as "tertiles") and the colon, all substantially equal in length, e.g., in terms of intestinal mucosal tissue displayed. The parsing may be performed based on identification of anatomical landmarks. Thus, identification of the first duodenal image can indicate entrance into the small bowel and identification of the first cecal image (or last terminal ileum image) can indicate entrance into the colon. The identification of one or more of such anatomical landmarks can be performed by a user, during a display of the received stream of images, and received as input by a computerized system, such as workstation 11 of FIG. 1 (e.g., via I/O device 22). Alternatively, the anatomical landmarks can be identified automatically by the computerized system (e.g., via processor 14 of FIG. 1). For example, entrance to the small bowel may be identified according to the methods and systems disclosed in U.S. Pat. No. 8,768,024 to Zinaty Ofra et al., entitled "System and method for real time detection of villi texture in an image stream of the gastrointestinal tract", assigned to the common assignee of the present application. Entrance to the colon can be identified according to the methods and systems disclosed in U.S. Pat. No. 8,922,633 to Pfeffer Yehuda, entitled "Method and system for detecting transition of in-vivo device between sections of the GI system", assigned to the common assignee of the present application.

The identified portion of the stream of images which shows the small bowel (i.e., from first duodenal image to first cecal image) can be then parsed into three segments, optionally substantially equal in length via a computerized assessment of the capsule endoscope's progress through the subject's GIT. Such computerized assessment may be based, for example, on the methods and systems disclosed in U.S. Pat. No. 8,792,691 to Krupnik et al., entitled "System and method for detecting motion patterns of in vivo imaging devices", assigned to the common assignee of the present application.

In a step 120, a set of values for each of the segments may be obtained. The set of values may refer to the pathological involvement of the segment in the disease and to the severity of the mucosal manifestation of the mucosal disease in the segment. In some embodiments, the set of values may at least refer to the severity of the mucosal manifestation of the mucosal disease in each segment. For example, in case of assessing an IBD patient, the mucosal manifestation may include lesions and strictures. In some embodiments, the obtained set of values for each segment may include a value indicating the highest degree of severity of the mucosal manifestation in the segment, a value indicating the typical or common degree of severity of the mucosal manifestation in the segment, and/or a value indicating the extent of the mucosal manifestation in the segment. In some embodiments, the most severe mucosal manifestation for a segment may not be representative of the typical or common severity of the mucosal manifestation in the segment. In this manner, having both the most severe mucosal manifestation value and the typical or common severity value can yield a more comprehensive picture of the mucosal manifestation of the disease in the segment. The degree of severity can be determined according to a value system. For example, in case of assessing lesions in a GIT of an IBD patient, the value system may include three degrees of severity: mild, moderate and severe or none denoted by 1, 2, 3 and 0, correspondingly. The extent value of a mucosal manifestation can indicate the portion of the mucosal tissue surface of the respective GI region displaying the mucosal manifestation of the disease. For example, in case of assessing an IBD patient, the extent value can indicate a percentage of a tissue surface of a GIT region that has a pathological mucosal involvement of the disease. In some embodiments, where IBD is assessed, the extent value may be none, less than 10 percent, between 10 and 30 percent, between 30 and 60 percent, or greater than 60 percent. This is since according to experience, the lower percentile ranges are more common with respect to manifestations of the disease.

In some embodiments, one or more values of the set of values may be obtained as input from a user for each segment. In some embodiments, one or more values of the set of values may be calculated for each segment via the computerized system. Thus, in some embodiments some of the values may be received as input from a user and the rest of the values may be calculated via the computerized system. In some embodiments, one or more values may be determined based on a combination of user input and calculations performed by the computerized systems and methods.

When one or more values is determined by a user, parsing the GIT portion into segments substantially equal in length may be more advantageous. Manual Assessment of segments substantially equal in length may ease and simplify the assessment process for the user. A more easy and simple manual assessment procedure may also lead to a more accurate manual assessment.

When at least a portion of the values or all of them are determined solely or in addition by the disclosed computerized systems and methods, parsing the GIT portion into segments not necessarily equal in length may be more advantageous. For example, parsing the GIT portion into segments at least partially corresponding to one or more anatomical regions of the GIT may be more beneficial for some disease assessments. In some embodiments, such unequal parsing of the segments may be desired during the assessing procedure, while, for example, in the final scores or overall evaluation, which is performed automatically (i.e., by computerized systems and methods), such unequal parsing may be weighted accordingly.

An exemplary method for calculating the exemplary set of values described above is herein disclosed. An ulcer detector may be used to identify ulcers. An exemplary ulcer detector is disclosed in U.S. Pat. No. 8,923,585 to Dori Peleg, entitled "Method and system for image-based ulcer detection", assigned to the common assignee of the present application. The ulcers may be then characterized in order to determine their degree. For example, the degree of the ulcer may be determined based on their size. The size of the ulcers may be estimated according to methods such as disclosed in International Publication No. WO 2015/049684 to Krupnik et at, entitled "System and method for size estimation of in-vivo objects", and U.S. Pat. No. 9,412,054 to Krupnik, entitled "Device and method for determining a size of in-vivo objects", each assigned to the common assignee of the present application. Functions for determining maximum and median, as known in the art, may be used to determine the most severe degree of the ulcers and the most common degree of the ulcers correspondingly in each segment. The extent value can be then determined based on the images identified as displaying ulcers in each segment and assessment of the capsule endoscope's progress through the subject's GIT in these specific images.

In some embodiments, the set of values can further refer to the pathological involvement of the mucosa in one or more portions of interest of the GIT. For example, the set of values may include values indicating the involvement or non-involvement of the duodenum, terminal ileum, right colon and/or left colon. Such information may affect the manner of treatment and medical management of a patient.

In a step 130, a representation indicating the severity and location of the mucosal manifestation of the mucosal disease in the entire imaged GIT portion (including the entire GIT) is generated, thus allowing the assessment of the condition of the mucosal disease in the subject's GIT portion. The representation is generated based on the obtained set of values for each segment. The representation can include one or more elements such as tables, graphs, reports, anatomical graphical representations and/or scores.

In some embodiments the representation may include anatomical graphical representation of the GIT portion depicting each of its GIT regions and one or more values of the obtained set of values for each of the regions. In some embodiments, the obtained set of values can include information indicating the location of the mucosal manifestation within each of the GIT regions (e.g., at the beginning or end of the region). In some embodiments, the representation may indicate such locations. For example, indication of the degree of the mucosal manifestation severity may be overlaid on the anatomical representation in a location relatively corresponding to the location of the mucosal manifestation within the GIT region. In some embodiments, colors may be used to indicate one or more of the values for each GIT region. In some embodiments, the anatomical representation may indicate the different GIT regions. For example, if the small bowel is parsed into three regions, the anatomical representation of the small bowel may be composed of three segments laid in parallel, as shown, e.g., in FIG. 8.

The location of the mucosal manifestation of the mucosal disease based on GIT regions can also refer to characteristics of the mucosal involvement of the GIT such as the mucosal manifestation distribution pattern. Thus, the location by GIT regions can indicate that the mucosal involvement is non-existent, focal, patchy, continuous or diffuse.

In some embodiments, the set of values may further include values referring to the mucosal involvement of sub-segments corresponding to sub-regions of the GIT. For example, the sub-regions may correspond to anatomically defined portions of the GIT, such as the duodenum, terminal ileum, right colon and left colon. Such values may include a binary value indicating if the sub-region is involved in the disease (i.e., displays mucosal manifestation).

Figure 2B:
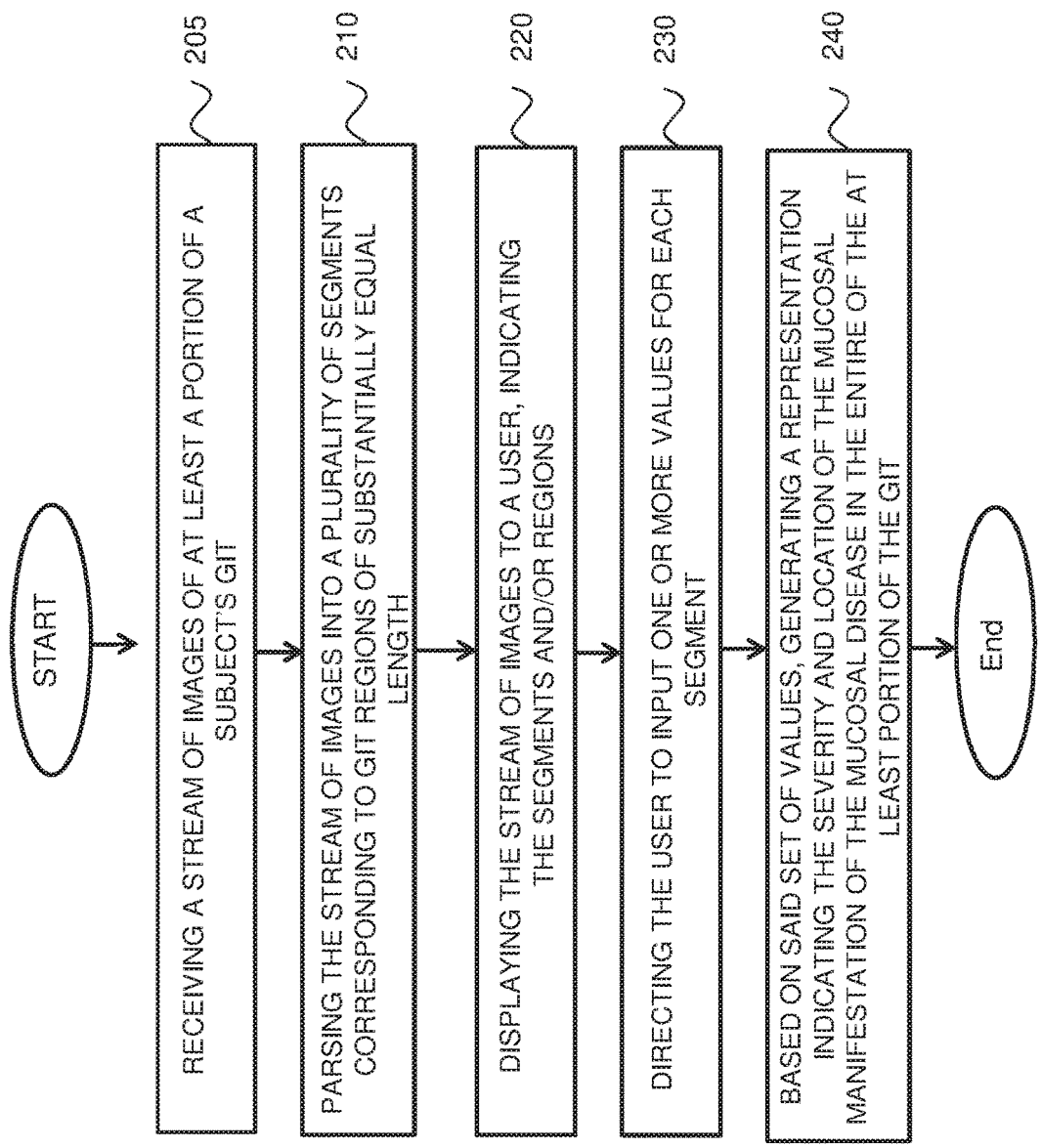
FIG. 2B is a flow chart for a method of mucosal assessment of a mucosal disease in a GIT of a subject, according to another illustrative embodiment of the invention.

FIG. 2B is a flow chart for assessment of a condition of a mucosal disease in a GIT of a subject (e.g., patient), according to another illustrative embodiment of the invention. This embodiment may be similar to the embodiments described with respect to FIG. 2A unless indicated otherwise. The method involves receiving a stream of images of the subject's GIT (Step 205).

The method also involves parsing at least a portion of the stream of images into a plurality of segments (Step 210). For example, a portion of the stream of images or the entire stream of images can be parsed into segments by segment display generator 24, as described above with respect to FIG. 1. The segments can correspond to GIT regions of substantially equal length. Thus, each segment can include a plurality of images showing a region of the GIT.

In some embodiments, the method also involves, for each segment of the plurality of segments, a) one or more images of the respective segment are displayed, b) one or a plurality of values is received that indicates the pathological involvement of the segment in the disease with respect to mucosal manifestation of the disease and the severity of the mucosal manifestation, based on the one or more images that are displayed, c) an output representation is generated that indicates to a user the severity and/or location of the mucosal manifestation of the mucosal disease for all segments. In this manner, it can be possible to minimize the amount of reviewing that is done by a user (e.g., a physician) to obtain a view of the severity and location of the mucosal disease for the entire GIT portion including all segments.

The stream of images is then displayed to the user, while indicating the segments and/or GIT regions in the displayed stream of images (step 220). In various embodiments the particular frames that are presented to the user for review of a particular segment is determined by the computer, for example, based on computer analysis of the stream of images.

The user can be then directed to input one or more values of the set of values for each of the segments (step 230).

For example, in some embodiments, the set of values may include a value indicating the most typical or common degree of severity and/or the highest degree of severity of a mucosal manifestation, e.g., lesions, in each segment. Lesion severity, for example inflammatory lesions, can be on a progressive spectrum, starting from a mild mucosal involvement of hyperemia and erosions, through aphthous ulcers and finally progressing to a larger deep ulcers that can lead to lumen stenosis and formation of strictures. Streams of images with active inflammatory involvement can often be characterized by a large number of mucosal manifestations, such as lesions. However, therapeutic decision making can benefit from indication of the most common mucosal manifestation and/or the most severe mucosal manifestation in a segment, rather than indicating every possible mucosal manifestation displayed in the segment. By assigning, e.g., a most common lesion value and/or a most severe lesion value to a segment, a reviewer (i.e., a user) can obtain lesion information regarding the segment, without having to consider each and every lesion in the segment.

In some embodiments, the user is directed to input the one or more values for each of the segments during and/or immediately after the display of the segment and prior to the display of the next segment. In some embodiments, the user may be compelled to input the one or more values for each segment prior to the display of the next segment, e.g., by refraining from displaying the next segment as long as the user input has not been received. The user may be prompted to provide an input. Inputting (i.e., by a user) the one or more values for each segment during the display of each segment and/or prior to the display of the next segment may shorten the assessment process, make it more efficient and more accurate. Thus, the user provides his input during his review of the stream of images and while it is still fresh in his mind and not influenced by other images, e.g., of a different segment.

For example, in some embodiments the user may be directed to provide the value of highest degree of severity during the display of each segment. The user may then identify an image depicting a first mucosal manifestation, for example, a first lesion, having a certain degree of severity during the display of a segment. The user may then review more attentively and/or indicate only the next image depicting a lesion which appears to have a higher degree of severity than the first lesion. Other images which depict other lesions that appear to have the same degree of severity or a lower one, do not require the user's attention. This process can be continued until either the segment images have been fully displayed or the maximal degree of severity has been assigned to an image depicting a lesion in the segment, which ever come first.

A representation can be then generated for the user based on the set of values. The representation can indicate to the user the location and severity of the mucosal disease in the entire portion of interest of the GIT (e.g., the small bowel and colon for IBD) (step 240). In some embodiments, an anatomical representation of the GIT is displayed, e.g., including the small bowel and the colon. In some embodiments, each segment with its corresponding set of values, e.g., the most common lesion severity value, the extent value and the most severe lesion value is displayed along its corresponding position (i.e., the corresponding GIT region) in the anatomical representation.

FIGS. 3-17 described herein below refer to an exemplary embodiment of the disclosed methods and systems in which the set of values is received from a user.

Figure 3:
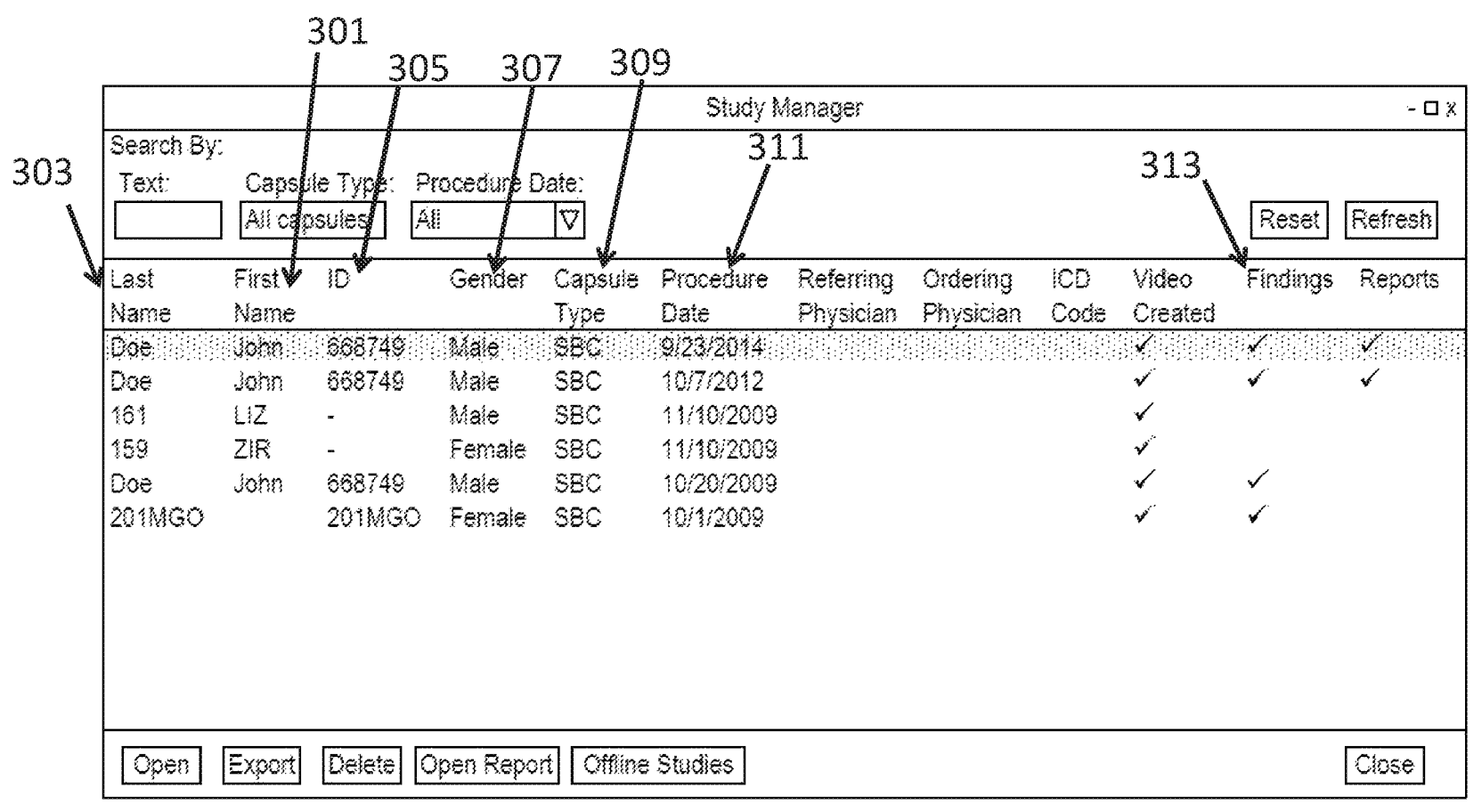

FIG. 3 is an exemplary screen shot of a start-up screen for a system for assessment of a condition of a mucosal disease in a GIT of a subject, according to an illustrative embodiment of the invention. A user can view all of the videos available in the system. Each available video is identified by a first name 301, last name 303, patient identifier 305, patient gender 307, capsule type ("type of capsule used to capture the video") 309, procedure date 311 (e.g., date the video was taken), findings 313, and other information regarding each available video.

Figure 4:
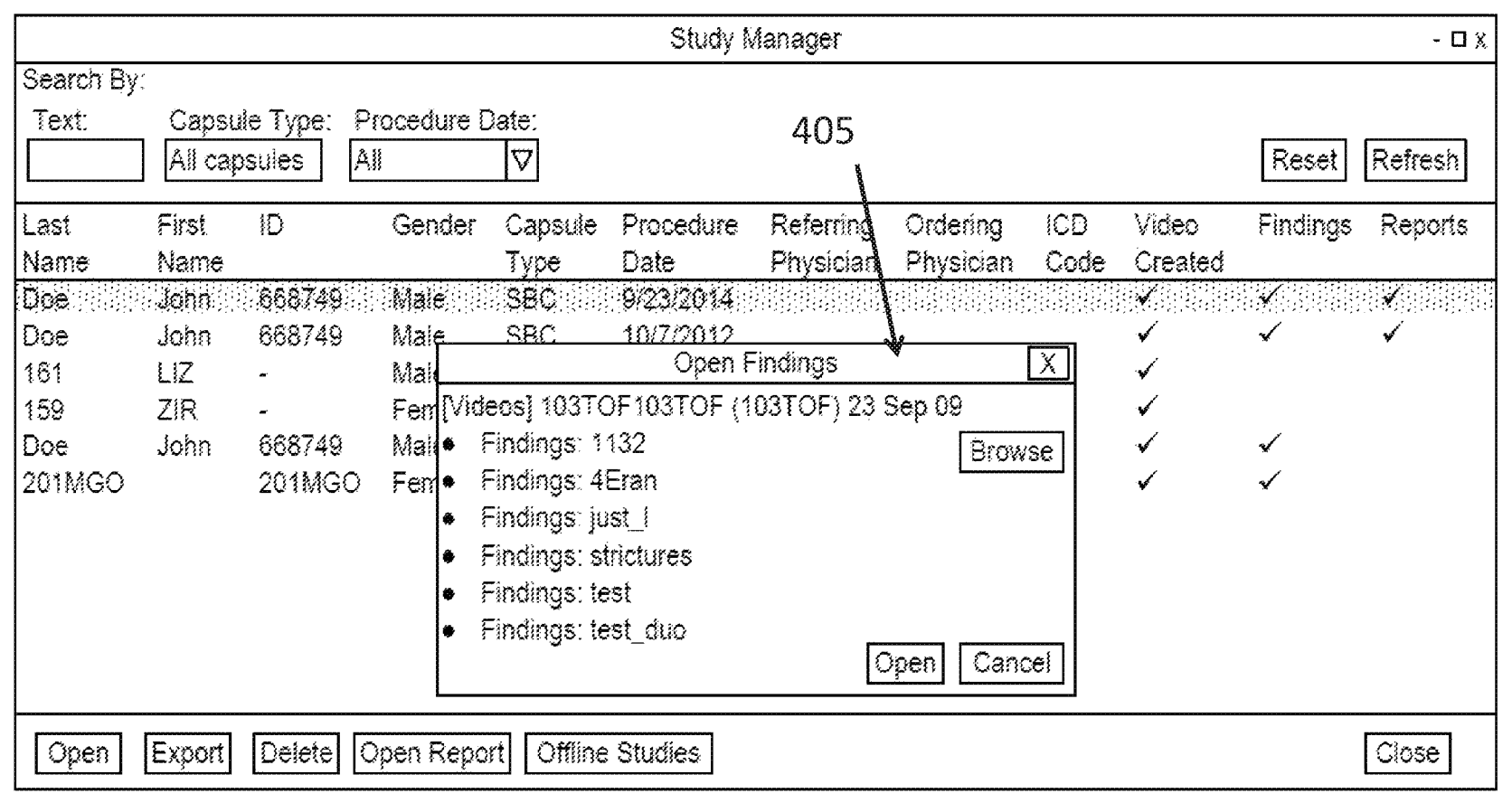

FIG. 4 is an exemplary screen shot of an exemplary list of findings 405 that can be presented to a user for any available video, according to an illustrative embodiment of the invention.

Figure 5:
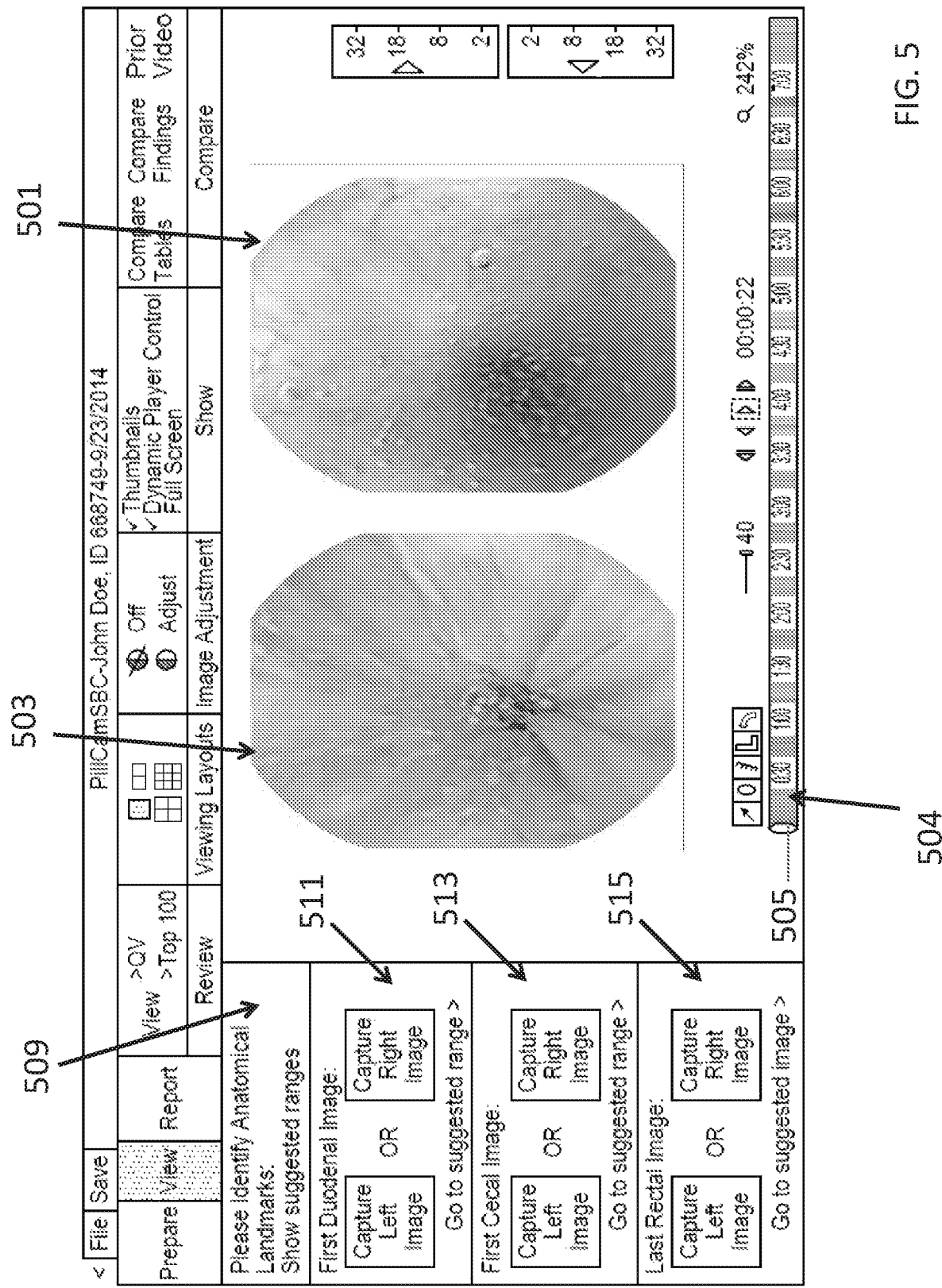
FIG. 5 is an exemplary screen shot of a start of a mucosal assessment of a mucosal disease for a selected video (e.g., images of a selected patient), according to an illustrative embodiment of the invention.

FIG. 5 is an exemplary screen shot of a start of an assessment of a condition of a mucosal disease for a selected video (e.g., images of a selected patient), according to an illustrative embodiment of the invention. In this embodiment, a right image 501 and left image 503 of images taken with a capsule that included two cameras are displayed. The particular images correspond to a position of marker 504 on a time bar 505. The time bar 505 allows a user to skip around the images. An indicator 509 is presented to the user to identify anatomical landmarks. Areas to input the anatomical landmarks on a GIT are presented to the user. In particular, a first duodenal image capture area 511, a first cecal image capture area 513, and a last rectal image capture area 515.

Each of the image capture areas, 511, 513, and 515, include instructions to the user to capture a left or right image, and a link to go to a suggested range of images. When a user clicks on the suggested range of images, marker 504 on the time bar 505 moves to a range of images that the system determines is likely the range matching that area. For example, if a user clicks on the go to a suggested range link in the first cecal image capture area 513, the marker 504 moves to a position on the time bar 505 to correspond to a time in the video where the first cecal image likely exists. The system may use a processing unit to determine the suggested ranges of images and according to the exemplary methods described above.

In some embodiments, shading of the time bar 505 indicates various image properties for groups of images in the video. In some embodiments, coloring of the time bar 505 indicates various image properties for groups of images in the video.

Figure 6:
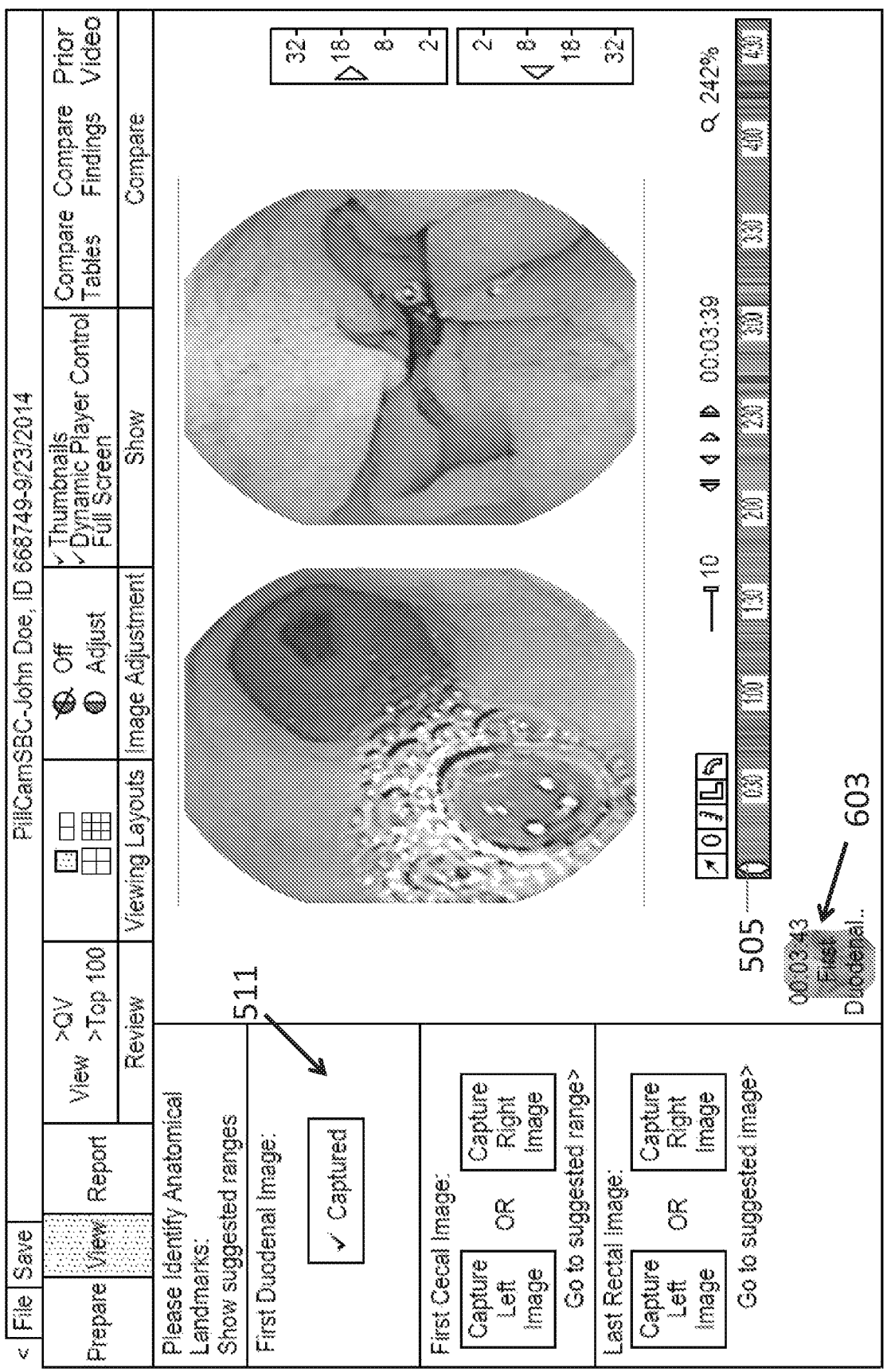
FIG. 6 is an exemplary screen shot of a capture of the first duodenal image, according to an illustrative embodiment of the invention.

FIG. 6 is an exemplary screen shot of a capture of the first duodenal image, according to an illustrative embodiment of the invention. Upon selection of an image by the user, a thumbnail 603 of the user's selection is created. The first duodenal image capture area 511 shows a captured indicator, to indicate that the duodenal image has been captured. The thumbnail is coupled to the time bar 505 such that the position of the thumbnail 603 in the video is discernable.

Figure 7:
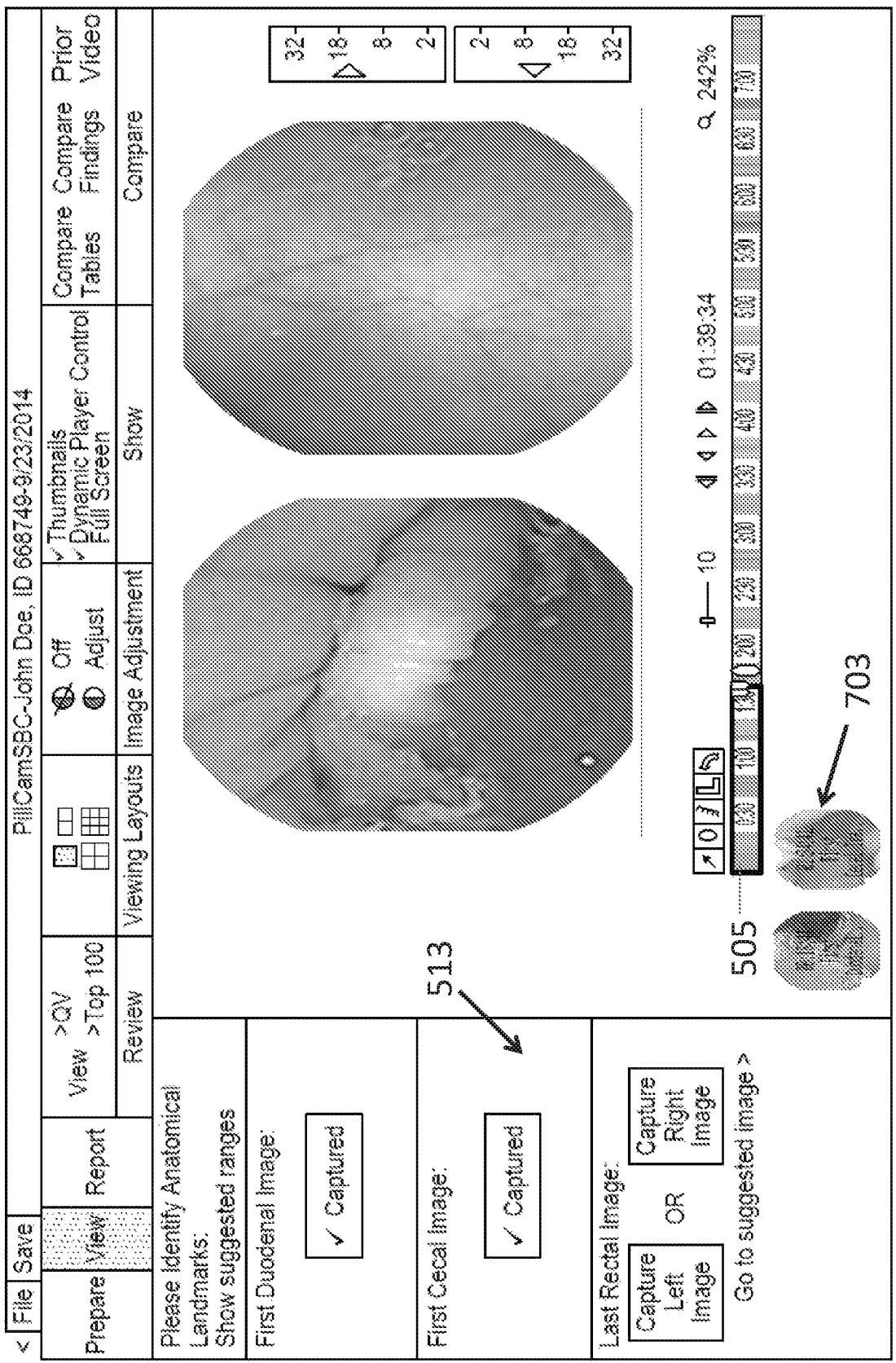
FIG. 7 is an exemplary screen shot of a capture of the first cecal image, according to an illustrative embodiment of the invention.

FIG. 7 is an exemplary screen shot of a capture of the first cecal image, according to an illustrative embodiment of the invention. Upon selection of an image by the user, a thumbnail 703 of the user's selection is created. The first cecal image capture area 513 shows a captured indicator, to indicate that the duodenal image has been captured. The thumbnail is coupled to the time bar 505 such that the position of the thumbnail 703 in the video is discernable.

Figure 8:
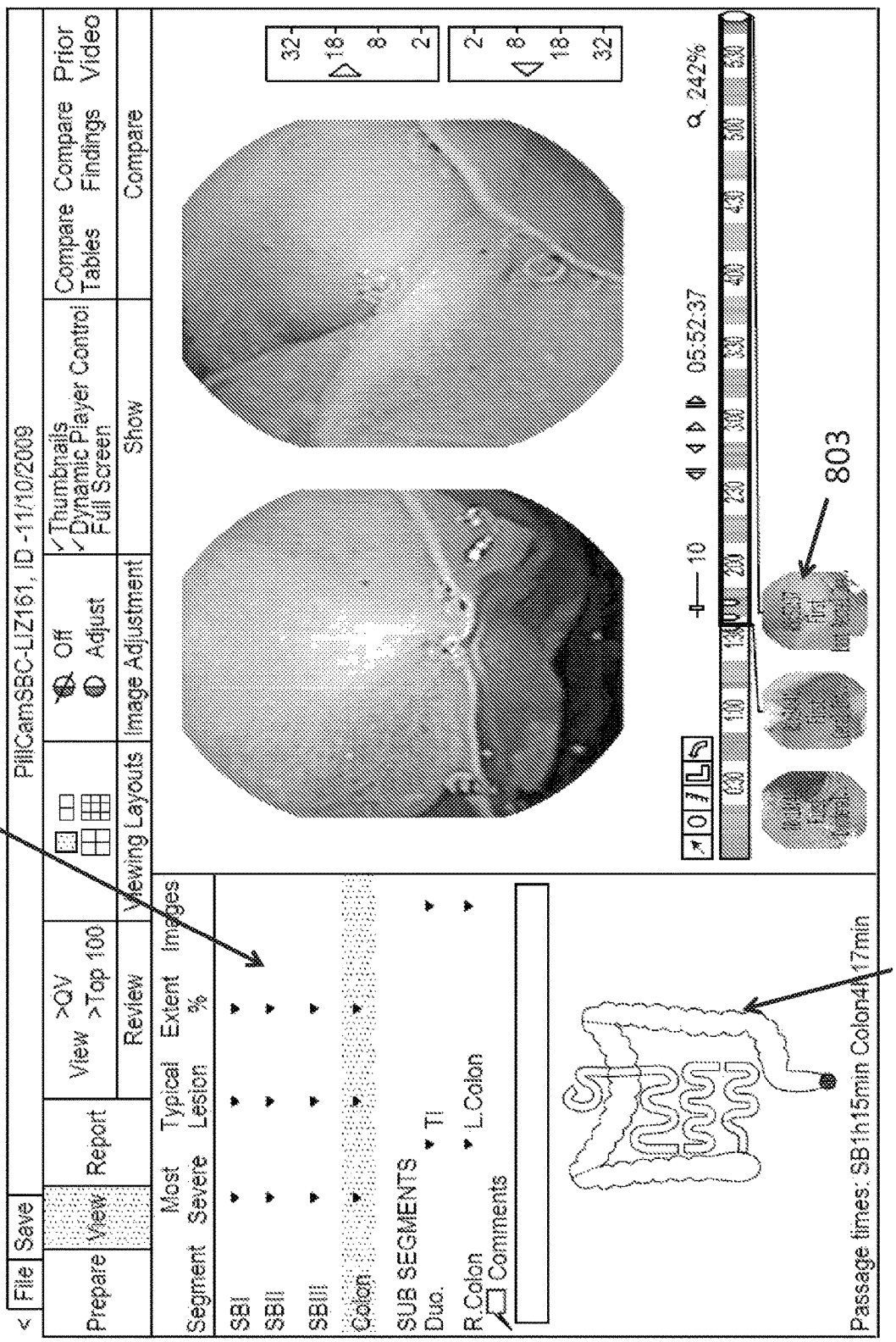
FIG. 8 is an exemplary screen shot after the capture of the last rectal image, according to an illustrative embodiment of the invention.

FIG. 8 is an exemplary screen shot after the capture of the last rectal image, according to an illustrative embodiment of the invention. Upon selection of an image by the user, a thumbnail 803 of the user's selection is created. The image capture areas as shown in FIGS. 6 and 7 is replaced by a segment value area 805, once all of the aforementioned anatomical landmarks have been identified and captured. Segment value area 805 may include, for example, a table, as shown in FIG. 8. The segment value area 805 includes four segments, SBI, SBII, SBIII and Colon. For each of the segments in the segment value area 805, a user can input values in accordance, for example, with FIG. 9-12, described below. In some embodiments, when a user inputs one of the values, the value automatically populates. Alternatively or additionally, a value calculated by the system may automatically populate. An anatomical graphical representation of the GIT of the subject 807 can be displayed.

Figure 9:
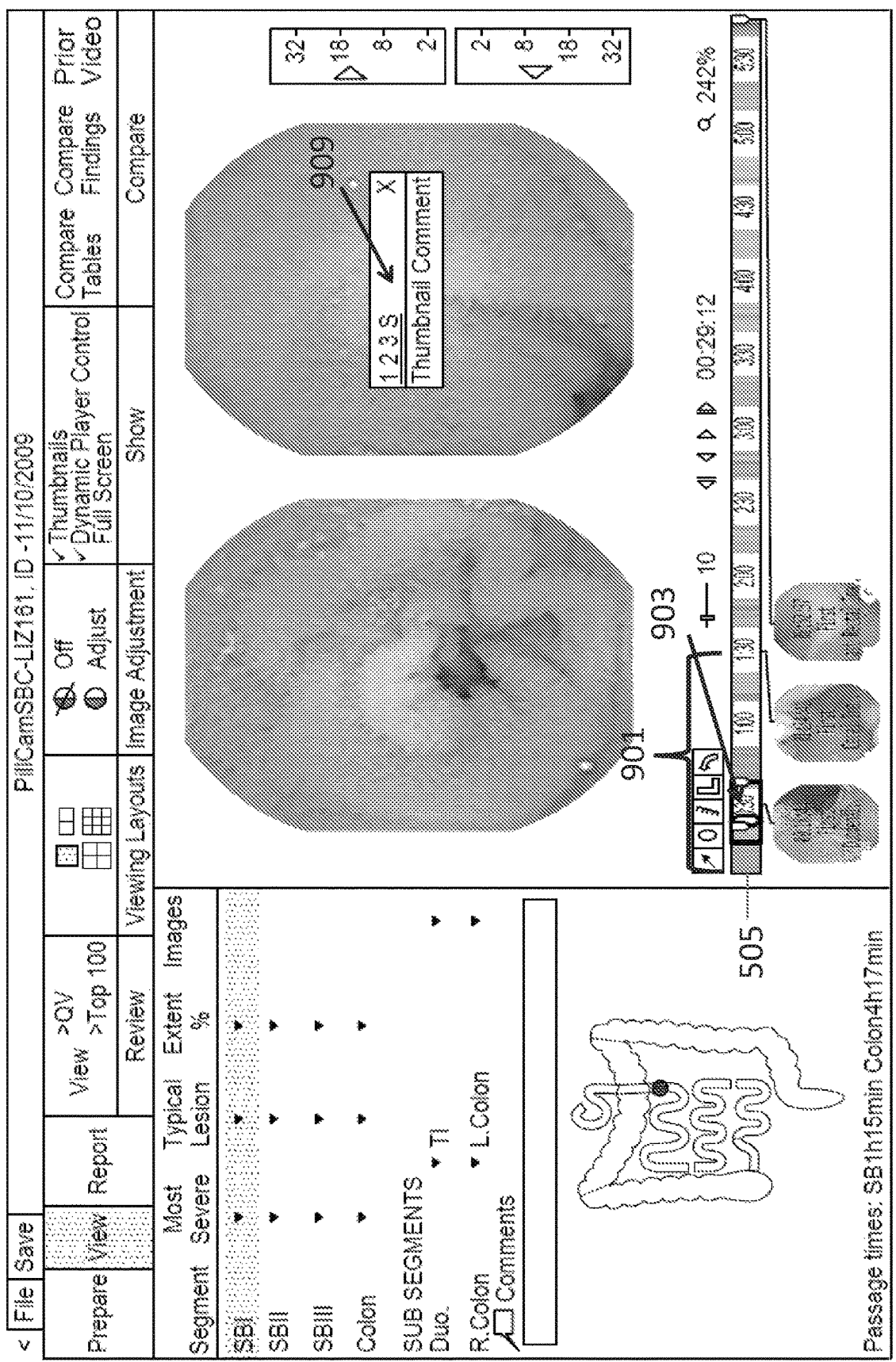
FIG. 9 is an exemplary screen shot of an exemplary mucosal assessment, according to an illustrative embodiment of the invention.
Figure 10:
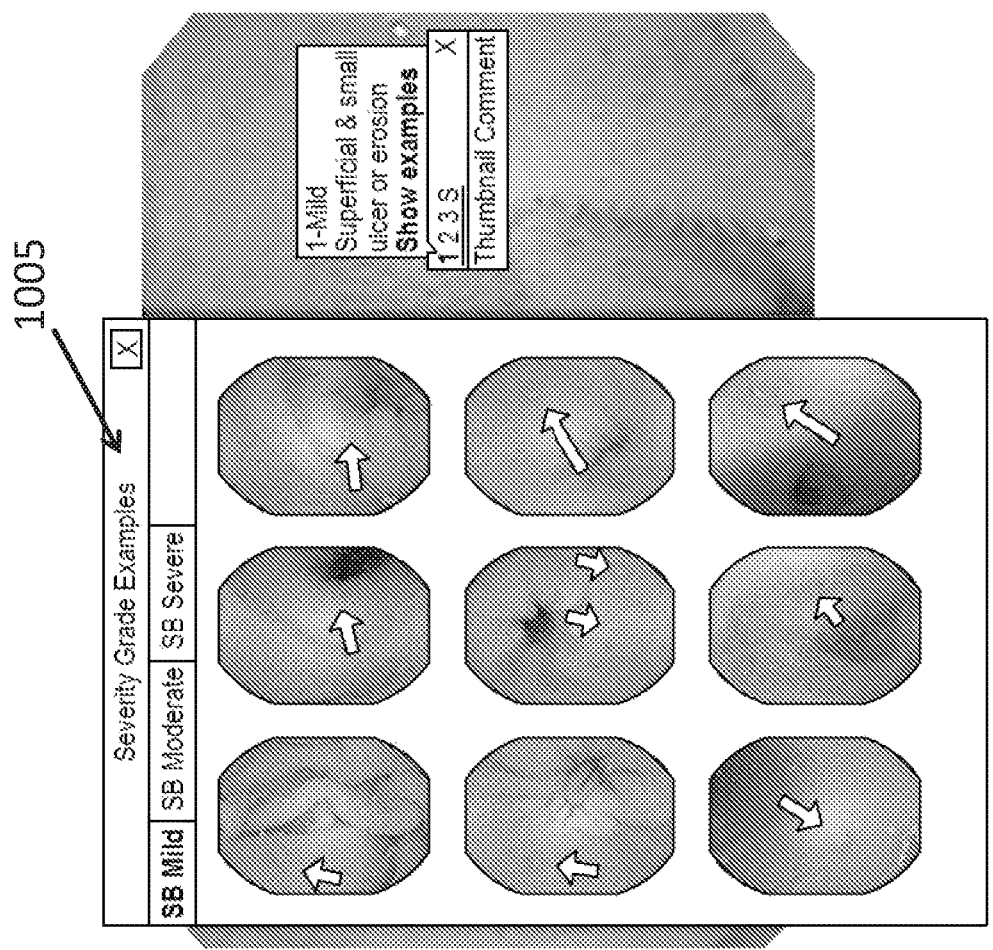
FIG. 10A and FIG. 10B are exemplary screen shots of an exemplary severity pop-up tool, according to illustrative embodiments of the invention.

FIG. 9 is an exemplary screen shot of exemplary segment assessment, according to an illustrative embodiment of the invention. The time bar 505 shows an anatomical segment of the image stream 901, i.e., corresponding to an anatomical portion of the GIT (e.g., a distance along the GIT between the first duodenal image and the first cecal image, i.e., the small bowel). The anatomical segment 901 is sub-divided into three segments substantially equal in length. In this example, each of the three small bowel segments is comparative to the colon in terms of length, and each of these four segments (i.e., three segments of the small bowel and the colon segment) is reviewed and assessed, as described above, in an independent and sequential fashion. As is shown in FIG. 9, a segment 903 of anatomical segment 901 is highlighted, and left and right images in segment 903 are displayed. When a first image displaying, e.g., a lesion, is identified (for example, by receiving an input from the user), the user is prompted via a graphical control element 909 to input a first lesion value for the segment 903. In some embodiments, the user can select to utilize a lesion severity pop-up tool by clicking within on graphical control element 909, as is shown in FIG. 10A and FIG. 10B. The lesion severity pop-up tool 1003 presents to the user examples of lesion severity grading (e.g., degrees) 1005. In this manner, a user can compare the left and right images of the segment 903 against examples in the lesion severity pop-up tool 1005 to determine a lesion severity value to assign to the segment 903. The examples can be pre-loaded. In some embodiments, a catalogue of images is provided to assist in generating a uniform and standardized grading and/or scoring, to for example, provide a standardized assessment.

Turning back to FIG. 9, in this embodiment, the most severe lesion values are between 1, 2, and 3. The values 1, 2 and 3 are relative values in that they denote severity relative to a scale, and other scales can be used.

The graphical control element 909 includes a thumbnail comment section that can allow the user to input a comment regarding the particular thumbnail.

FIGS. 12A-12D are exemplary screen shots of exemplary segment mucosal assessment, according to an illustrative embodiment of the invention. For each segment, upon completion of inputting the most severe lesion value, the user is prompted with a graphical control element 1203 for inputting the most typical or common lesion and the extent values for the segment. Graphical control element 1203 allows the user to select a typical or common lesion value for the segment (e.g., 0-3 as shown in pulldown menu 1205), and an extent value (e.g., percent ranges as shown in pulldown menu 1207). In some embodiments, unless the user inputs the typical or common lesion and extent values, the system can refrain from moving the user forward in the assessment process, by for example, displaying the pop-up window 1209 that requests that the user "please complete segment evaluation".

Once the user inputs the values for segment 903, the next segment in anatomical segment 901 is evaluated, as is described, for example, in FIG. 13 below.

Figure 11:
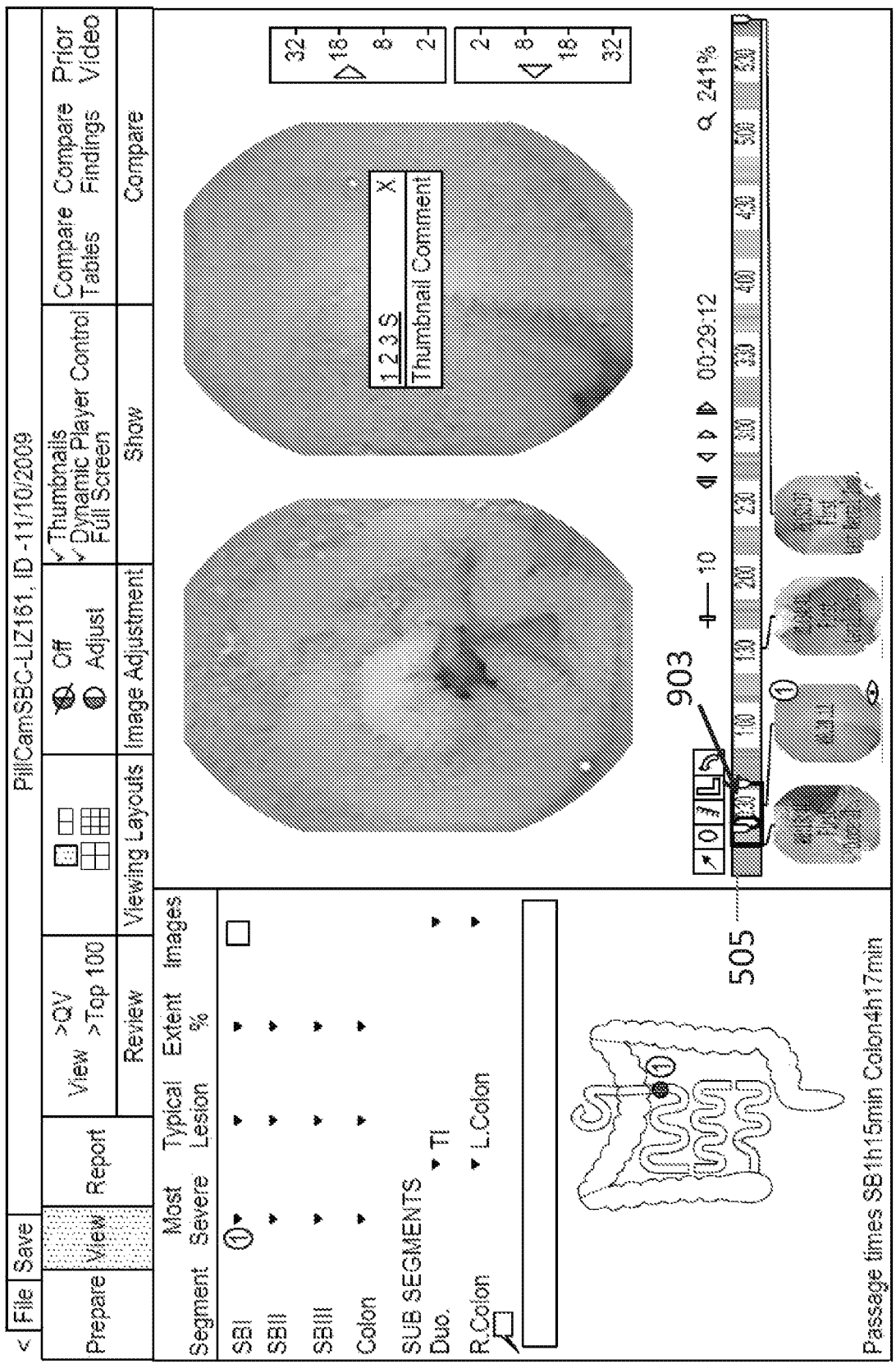
FIG. 11 is a further exemplary screen shot of the exemplary assessment of FIG. 9.
Figures 12A, 12B, 12C, 12D:
FIGS. 12A-12D are exemplary screen shots of exemplary mucosal assessments, according to an illustrative embodiment of the invention.

FIG. 11 is a further exemplary screen shot of the exemplary assessment of FIG. 9. FIG. 11 shows a screen shot of the assessment process as shown in FIG. 9 after a most severe lesion value for segment 903 has been received and entered. The time bar 505 shows segment 903 as highlighted, and the user input for the segment is displayed to the user. The user now can input another most sever lesion value for segment 903, if the degree of severity of another identified lesion in the segment is greater than the degree of severity of the already entered lesion value. In this manner each segment is evaluated for the most severe lesion. Once the user inputs the values for the segment 903, the next segment is evaluated in a sequential and independent manner, until all relevant segments have been reviewed and assessed, as is described, for example, in FIG. 13 below.

Figure 13:
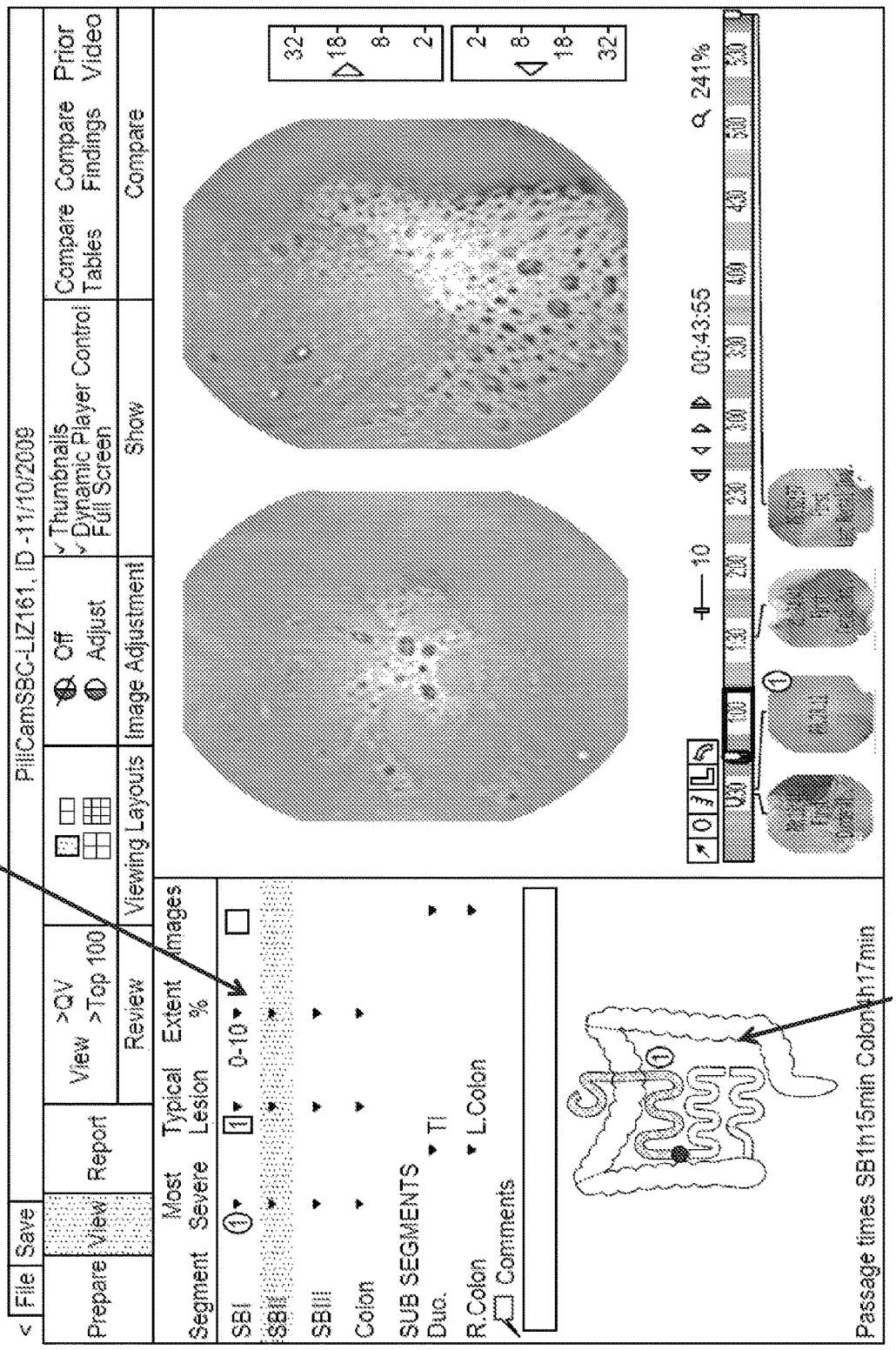
FIG. 13 is an exemplary screen shot of an exemplary mucosal assessment upon completion of assessment of the first segment, according to an illustrative embodiment of the invention.

FIG. 13 is an exemplary screen shot of segment assessment upon completion of assessment of the first segment, according to an illustrative embodiment of the invention. The segment value area 805 includes a table displaying the values input by the user as a result of the segment assessment, for example, as described in FIG. 9-12. The graphical representation of the GIT 807 displays the first segment with its corresponding most severe lesion value and its most common or typical lesion value. In this example, the most severe lesion value is indicated by a circle icon containing the severity value (in this example: "1") placed adjacent to the corresponding GIT region. The typical or common severity value is indicated by a fill color of the corresponding GIT region. Different or additional indicators that correspond to the values input by the user and/or calculated by the disclosed computerized systems and/or methods can be displayed. In some embodiments, the set of values may include one or more binary values, e.g., indicating the existence of a stricture in the segment or the involvement of sub-segments in the disease, as will be elaborated with respect to FIG. 14 below.

Figure 14:
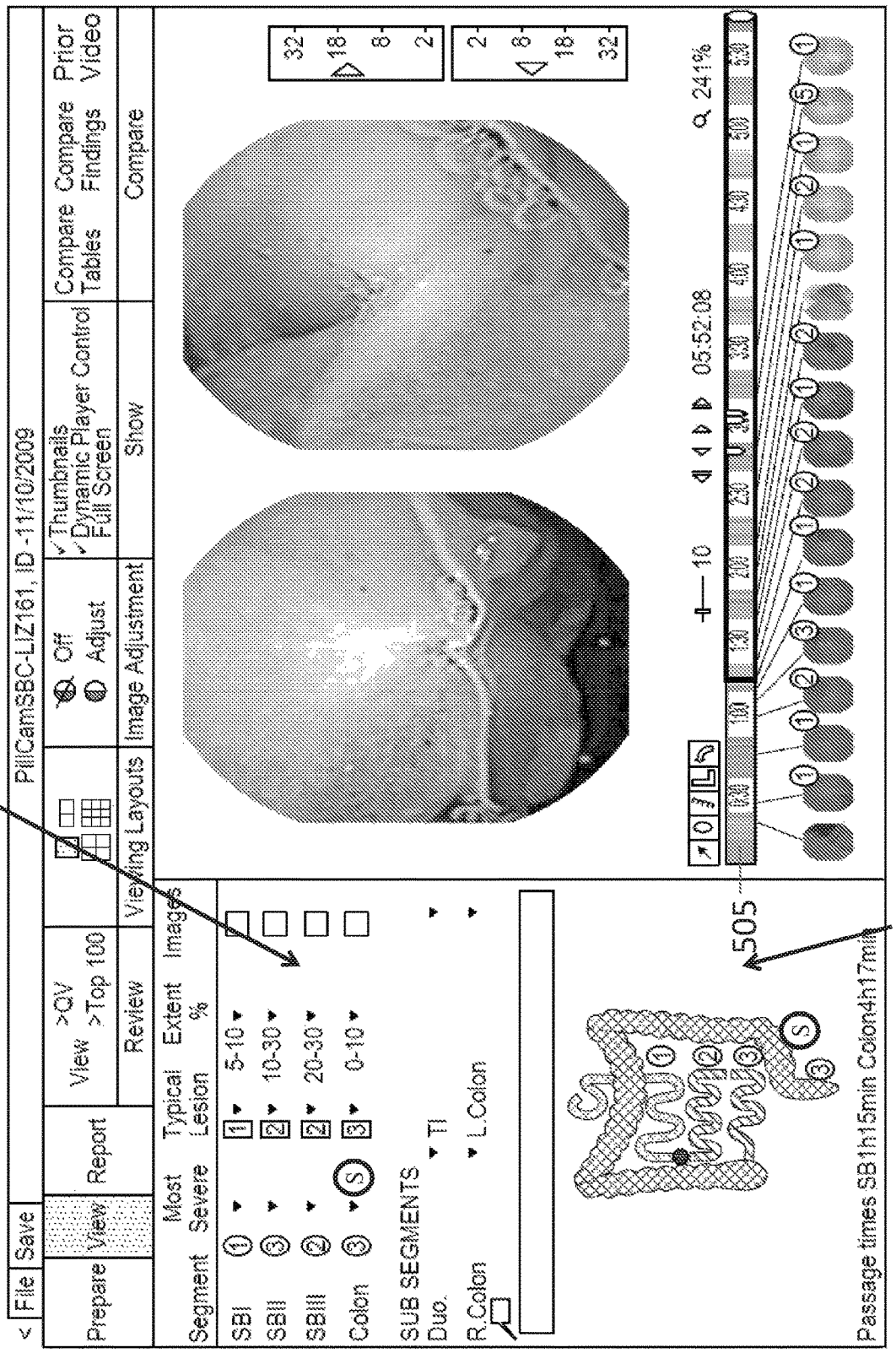
FIG. 14 is an exemplary screen shot of an exemplary mucosal assessment upon completion of assessment of all the segments, according to an illustrative embodiment of the invention.

FIG. 14 is an exemplary screen shot of segment assessment upon completion of assessment of all the segments, according to an illustrative embodiment of the invention. The segment value area 805 displays the values input by the user and/or by the disclosed computerized systems and/or methods, as a result of segment analysis of each of the segments. The images that were viewed and assigned values are displayed below the time bar 505 as thumbnails. The graphical representation of the GIT 807 displays each segment with its corresponding most typical or common lesion value and most severe lesion value. In some embodiments, the most common lesion values are assigned a color, e.g., a GIT region fill color. For example, the most common lesion value number one can be yellow, the most common lesion value number two can be orange and the most common lesion value number three can be red. In this manner, assessment information can be displayed in a manner that swiftly and easily conveys the assessment information to a user.

In some embodiments, the set of values may include binary values which indicate, for example, the existence of a stricture or the involvement of specific sub-segments corresponding to sub-regions of interest, such as the duodenum, the terminal ileum, the right colon and the left colon. As shown in FIG. 14, the received input includes the existence of a stricture in the colon segment (indicated in segment value area 805 by an icon containing the letter "s"). Accordingly, graphical representation of the GIT 807 includes an icon containing the letter "S" located adjacently to the colon region.

Figure 15A:
FIG. 15A and FIG. 15B are exemplary mucosal assessment reports that include data referring to uninvolved anatomical portions of the GIT, according to an illustrative embodiment of the invention.
Figure 15B:
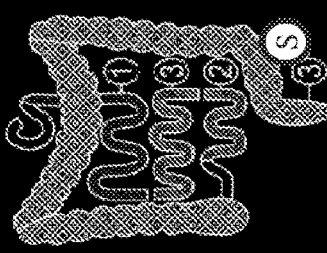

FIG. 15A and FIG. 15B are exemplary mucosal assessment reports that include data referring to involved or uninvolved anatomical portions of the GIT, according to an illustrative embodiment of the invention. Each report includes a table and a graphical representation of the GIT, presenting a mucosal assessment of the GIT and according to the embodiments shown in the previous Figures, such as FIG. 14. Each table presents input received. The sub-segments include the following anatomical portions: duodenum, terminal ileum, right colon and left colon. According to the report shown in FIG. 15A, the duodenum and terminal ileum are not involved. According to the report shown in FIG. 15B, only the right colon is not involved. The sub-segments not involved in the disease are indicated in the GIT graphical representations by not including a fill color (or alternatively, including a white fill color). On the other hand, the rest of the corresponding segments (i.e., excluding the not involved sub-segment), which is involved, has a fill color indicating the typical or common severity of the lesions in the respective segment.

Figure 16:
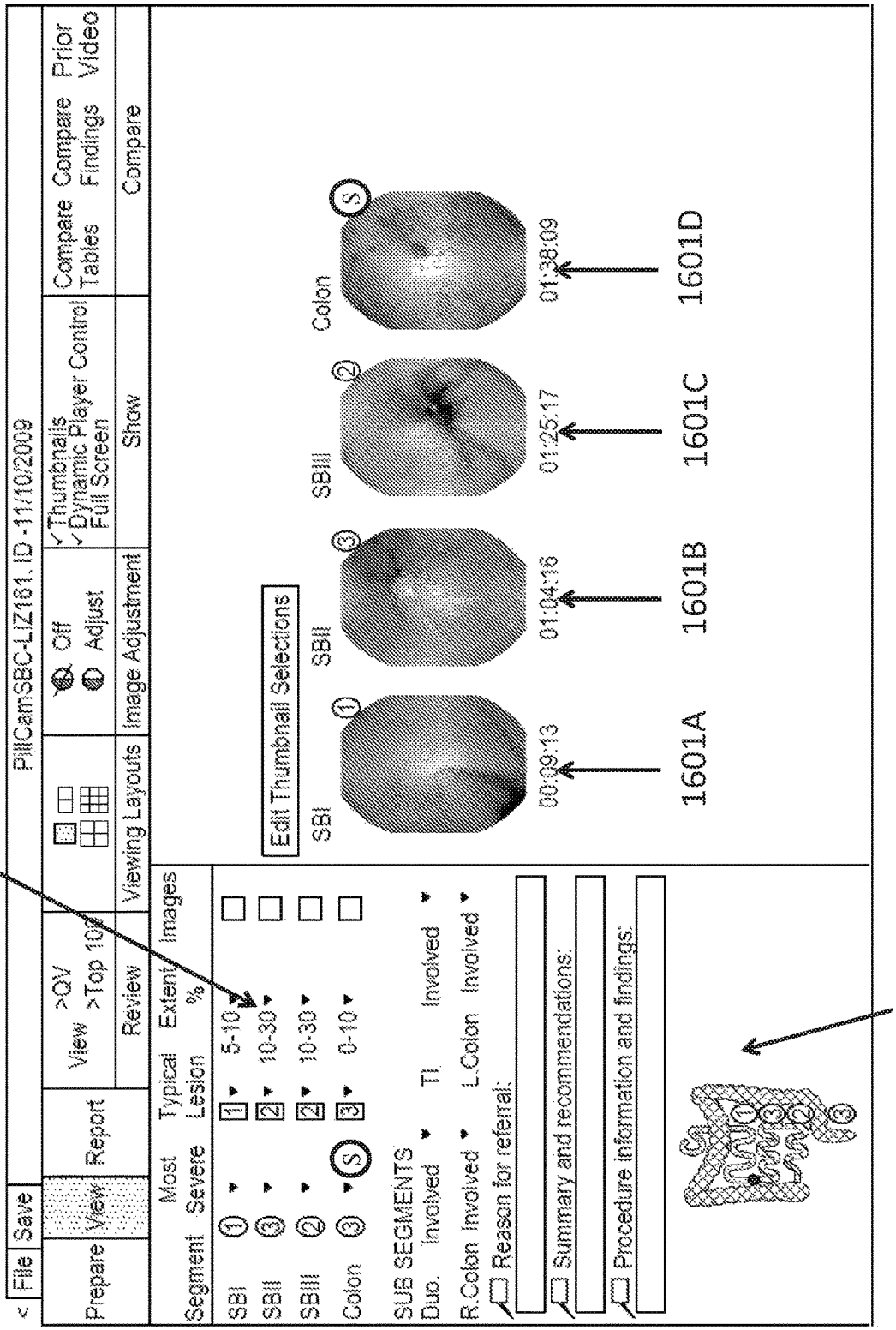
FIG. 16 is an exemplary screen shot of a GIT mucosal assessment upon completion of assessment of all the segments, according to an illustrative embodiment of the invention.

FIG. 16 is an exemplary screen shot of a GIT (or a portion of it) assessment upon completion of assessment of all the segments, according to an illustrative embodiment of the invention. The segment value area 805 displays the values input by the user and/or by the disclosed computerized methods and/or systems as a result of segment analysis of each of the segments. The anatomical graphical representation of the GIT 807 displays each segment with its corresponding values. The images 1601A through 1601C of the most severe lesion in each segment are displayed and image 1601D of a stricture.

Figure 17:
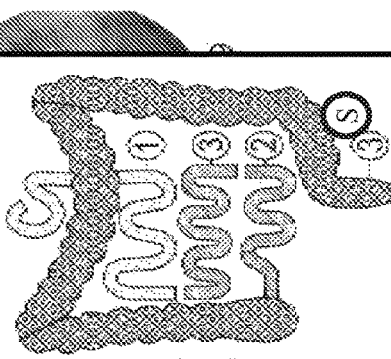
FIG. 17 is an exemplary screen shot of a printable report of GIT mucosal assessment upon completion of assessment of all the segments, according to an illustrative embodiment of the invention.

FIG. 17 is an exemplary screen shot of a printable report 1701 of a GIT assessment upon completion of assessment of all the segments, according to an illustrative embodiment of the invention.

FIG. 18 is an exemplary screen shot of two assessment reports for the same patient for procedures done on two different dates, according to an illustrative embodiment of the invention. The two assessment reports may be displayed in an adjacent manner, thus allowing a caregiver to better evaluate, assess and/or understand the progression or course of the disease in the subject's GIT and to better treat it.

Figure 19:
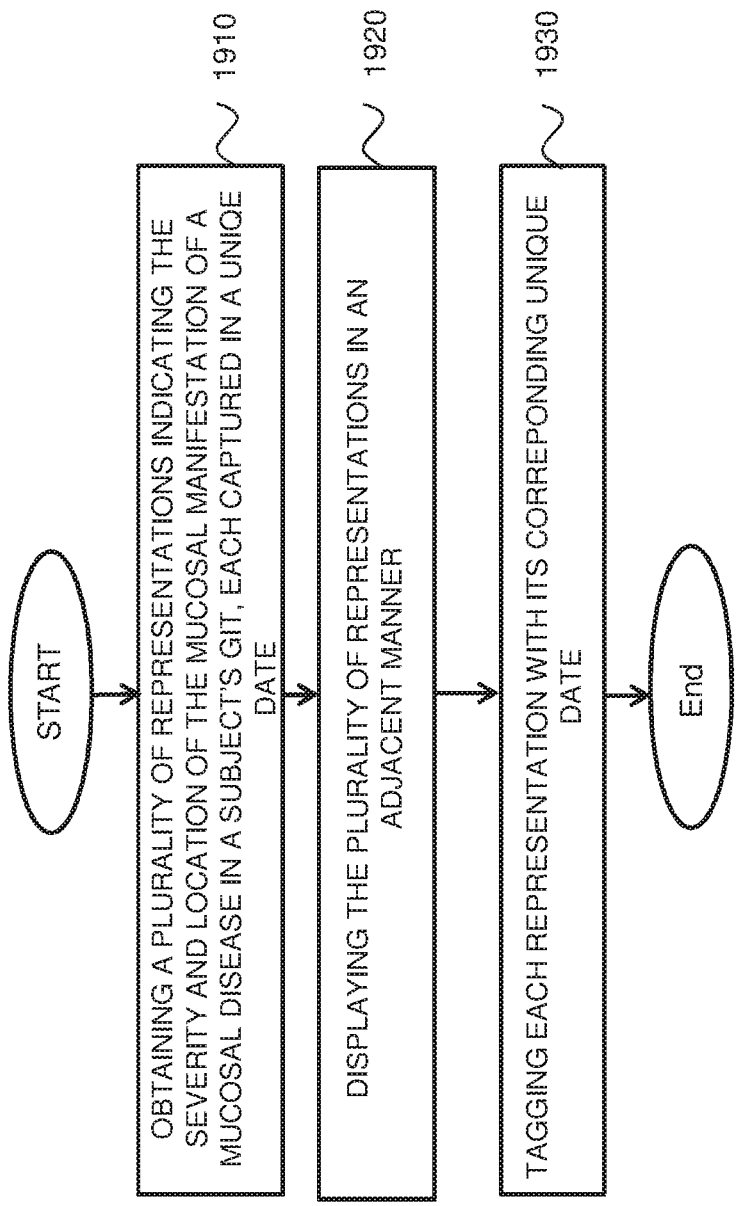
FIG. 19 is a flow chart for a method for monitoring mucosal manifestation of a mucosal disease in a subject's GIT, according to an illustrative embodiment of the invention.

FIG. 19 is a flow chart for a method for monitoring mucosal manifestation of a mucosal disease in a subject's GIT, according to an illustrative embodiment of the invention.

In a step 1910, a plurality of representations indicating the location and severity of the mucosal manifestation of a mucosal disease in at least a portion of a subject's GIT is obtained. Each representation of the plurality of representations can be generated according to the methods and/or by the systems disclosed herein. Each representation can be based on a stream of images captured in the subject's GIT during a procedure having a unique date. The subject can have a unique subject identifier. For example, the plurality of values can be for a patient having a unique identifier as patient 0001, having a procedure of a capsule endoscopy, on unique dates of Jan. 1, 2016, and Feb. 1, 2016. It is apparent to one of ordinary skill in the art that the patient identifier, dates and procedure are examples for discussion purposes only and that any number of procedures and dates can be included in the plurality of values.

In a step 1920, the plurality of representations is displayed in an adjacent manner.

In a step 1930, each representation can be tagged with its corresponding unique date, thus allowing a user to monitor the condition of the mucosal disease through time.

In some embodiments, each representation may include an anatomical graphical representation of the portion of the GIT depicting each of its GIT regions and one or more values of the obtained set of values for each of the GIT regions. The anatomical graphical representations may be displayed along a timeline according to their corresponding unique dates.

In some embodiments, the disclosed computerized methods and/or systems may be further utilized to compare the set of values assigned to the plurality of procedures performed in a patient GIT during a period of time and to present to the user the results of such comparison. Such comparison may be performed according to methods known in the art.

In some embodiments, relevant medical history data for the subject including informative descriptors (e.g. dates, procedure names, etc.) may be received. The plurality of representations may be then displayed along a timeline according to their corresponding unique dates. At least a portion of the patient medical history data may be also displayed along the timeline. In some embodiments, the method may further involve receiving medical treatment history data, including a treatment start and stop data, surgical history data and laboratory and physiological history or any combination thereof for the subject. The method may then further involve displaying along the timeline at least a portion of such data (as described, for example, in FIGS. 20A and 20B). The method can also involve receiving a request to view data for the subject. The request can include a unique subject identifier.

FIG. 20A and FIG. 20B are exemplary reports 2003 and 2005, each including multiple anatomical graphical representations and corresponding medical treatment along a timeline, according to an illustrative embodiment of the invention. For each report, anatomical graphical representations, 2007A-C and 2009A-C, of a portion of the GIT (i.e., the intestinal tract) of the same patient are displayed for assessments based on procedures done on three different times. Each graphical representation is shown on a timeline that also displays the patient's medical treatment over time. In this manner, a user can determine, inter alia, the effect that treatment has had for a given patient over time.

Figure 21A:
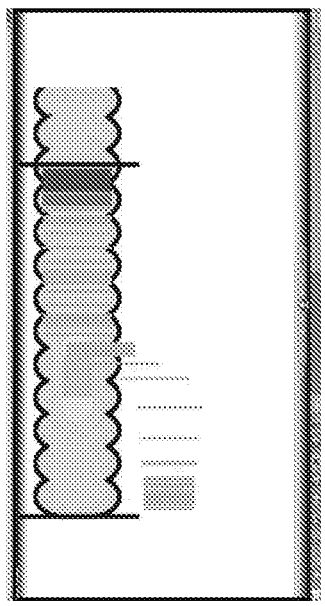
FIG. 21A, FIG. 21B and FIG. 21C are screen shots of an animation displaying a lesion heat map of a GIT region according to an illustrative embodiment of the invention.
Figure 21B:
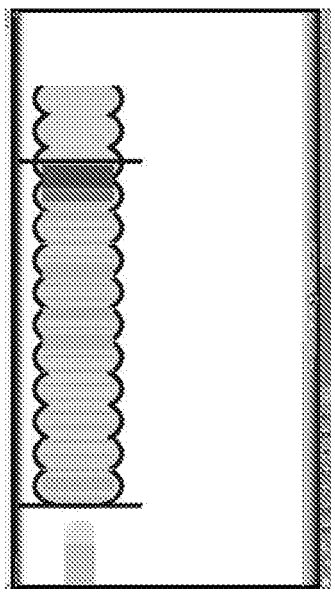
Figure 21C:
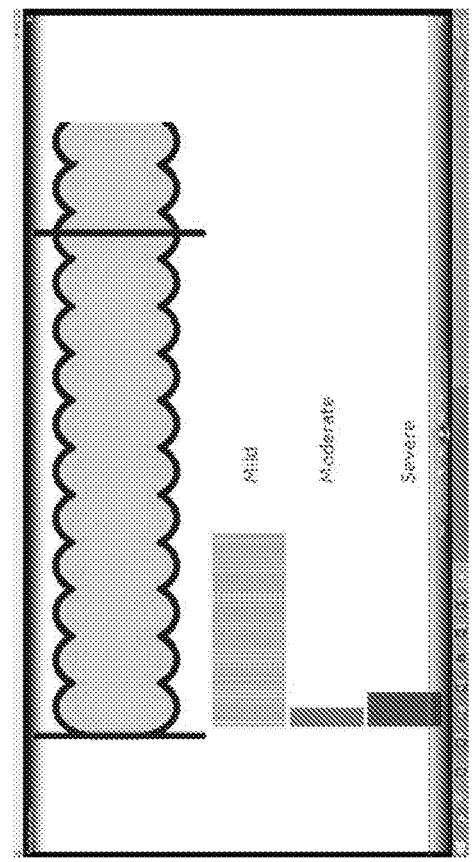

In some embodiments, wherein the mucosal manifestation can be identified and optionally assessed, at least partially, in an automatic manner, a presentation indicating the automatically identified mucosal manifestation may be presented to the user. In such embodiments, the disclosed systems and methods may be utilized to automatically identify mucosal manifestation in a stream of images of a GIT portion, as elaborated herein above. In some embodiments, the disclosed systems and methods may be further utilized to determine the degree of severity of the identified mucosal manifestation (e.g., mild, moderate or severe). In some embodiments, a map showing all of the automatically identified mucosal manifestations in one or more of the GIT regions may be generated and displayed to the user. For example, a heat map may be displayed including plurality of elements representing the identified mucosal manifestation in a GIT region colored according to their severity value. Reference is now made to FIG. 21A, FIG. 21B and FIG. 21C, which are screen shots displaying a lesion heat map of a GIT region according to an illustrative embodiment of the invention. A series of elements, wherein each element represents an identified lesion in a GIT region, may be presented according to the relative location of the lesions along the region. Each element may be then colored according to its automatically assessed severity level (e.g.: mild, moderate or severe), as shown in FIG. 21A. Based on such a map, the user may manually determine other values of the set of values with ease and in a prompt manner. For example, a user presented with the lesion heat map described above may determine, based on this map, values such as the most common lesion value, the most severe lesion value and the extent of involvement for the displayed region. FIG. 21C presents the lesions according to their color and indicates the corresponding severity level. Such presentation may further facilitate the manual determination of, for example, the most common, most severe and extent values in the GIT region. In some embodiments, presentation of the automatically identified mucosal manifestation and/or automatic assessment of such, may be used as a suggestion and/or to validate and/or to complete identification and/or assessment performed by a user.

In the preceding description, various aspects of the invention are described. For purposes of explanation, specific configurations and details are set forth in order to provide a thorough understanding of the invention. However, it is apparent to one skilled in the art that the present invention can be practiced without the specific details presented herein. Furthermore, well known features can be omitted or simplified in order not to obscure the invention.

Unless specifically stated otherwise, as apparent from the preceding discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Different embodiments are disclosed herein. Features of certain embodiments can be combined with features of other embodiments; thus certain embodiments can be combinations of features of multiple embodiments.

Embodiments of the invention can include an article such as a computer or processor readable non-transitory storage medium, such as for example a memory, a disk drive, or a USB flash memory encoding, including or storing instructions, e.g., computer-executable instructions, which when executed by a processor or controller, cause the processor or controller to carry out methods disclosed herein. In some embodiments, a computer processor or computer controller, e.g., data processor 14, can be configured to carry out embodiments of the invention, for example by executing software or code stored in a memory connected to the processor, and/or by having dedicated circuitry.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A computerized-method for a mucosal assessment of a mucosal disease in a Gastrointestinal Tract (GIT) of a subject, the method comprising:
receiving a stream of images of at least a portion of the subject's GIT;
parsing the stream of images into a plurality of segments, wherein each segment of the plurality of segments corresponds to a region of the at least portion of the subject's GIT;
obtaining a set of values for each segment of the plurality of segments, wherein for each segment, the respective set of values refers to pathological involvement of the respective segment in the mucosal disease and to severity of mucosal manifestation of the mucosal disease in the respective segment, the set of values for each segment obtained by, for each segment:
providing a user interface screen indicating the respective segment,
causing the user interface screen to display images from the stream of images that are part of the respective segment while the respective segment is indicated on the user interface screen,
causing the user interface screen to display a graphical control element having a plurality of selectable values while the images that are part of the respective segment are displayed, and
receiving at least one value of the respective set of values for the respective segment, via the graphical control element, by a user selection of one of the plurality of selectable values; and
based on the set of values for each segment, generating, in the user interface screen, a representation indicating location and severity of the mucosal manifestation of the mucosal disease in the entirety of the at least portion of the subject's GIT, thereby allowing to assess the condition of the mucosal disease in the at least portion of the subject's GIT.

2. The computerized-method of claim 1, wherein the GIT regions are of a substantially equal length.

3. The computerized-method of claim 2, wherein obtaining the set of values for each segment of the plurality of segments comprises directing the user to input the one or more values for the respective segment during or immediately after its display and prior to the display of the next segment.

4. The computerized-method of claim 1, wherein the at least portion of the GIT comprises the small bowel and the colon.

5. The computerized-method of claim 4, wherein the stream of images is parsed into four segments corresponding to three regions of the small bowel and the colon.

6. The computerized-method of claim 1, wherein the set of values obtained for each segment comprises:
i) a value indicating the highest degree of severity of the mucosal manifestation in the segment,
ii) a value indicating the common degree of severity of the mucosal manifestation in the segment, and
iii) a value indicating the extent of the mucosal manifestation in the segment.

7. The computerized-method of claim 6, wherein the extent value of a mucosal manifestation indicates the portion of the tissue surface of the respective GI region displaying mucosal manifestation.

8. The computerized-method of claim 1, wherein the stream of images is captured by a capsule endoscope and wherein the at least portion of the stream of images is parsed into a plurality of segments via a computerized assessment of the capsule endoscope's progress through the subject's GIT.

9. The computerized-method of claim 1, wherein the representation comprises an anatomical graphical representation of the at least portion of the GIT depicting each of its GIT regions and one or more values of the obtained set of values for each of said GIT regions.

10. The computerized-method of claim 1, wherein the obtaining of the set of values for each of said segments comprises identifying mucosal manifestation of the mucosal disease in said each of said segments.

11. The computerized-method of claim 1, wherein the obtaining of the set of values for each of said segments comprises calculating one or more values of the set of values for each of said segments.

12. The computerized-method of claim 1, wherein the set of values further refer to the pathological involvement of one or more portions of interest of the GIT.

13. A computerized-method for monitoring a mucosal disease in a subject's Gastrointestinal Tract (GIT), the computerized method comprising:
   obtaining a plurality of representations indicating the location and severity of mucosal manifestation of the mucosal disease in at least a portion of the subject's GIT, wherein each representation of the plurality of representations is generated according to the computerized-method of claim 1, and wherein each representation of the plurality of representations is based on a stream of images captured in the subject's GIT during a procedure having a unique date; and
   displaying the plurality of representations of the at least portion of the subject's GIT in an adjacent manner; and
   tagging each representation with its corresponding unique date, thereby allowing a user to monitor the condition of the mucosal disease through time.

14. The computerized-method of claim 13 wherein each representation comprises an anatomical graphical representation of the at least portion of the GIT depicting each of its GIT regions and one or more values of the obtained set of values for each of said GIT regions, and wherein the anatomical graphical representations are displayed along a timeline according to their corresponding unique dates.

15. The computerized-method of claim 14 further comprising:
   receiving medical treatment history data for the subject comprising a treatment start and stop data;
   displaying the plurality of representations along a timeline according to their corresponding unique dates; and
   displaying along the timeline at least a portion of the medical treatment history data.

16. The computerized-method of claim 15, wherein the medical treatment history data comprises medication prescribed to the subject.

17. A system for a mucosal assessment of a mucosal disease in a Gastrointestinal Tract (GIT) of a subject, the system comprising:
   a processor-readable medium having stored thereon instructions for:
   receiving a stream of images of at least a portion of the subject's GIT;
   parsing the stream of images into a plurality of segments, wherein each segment of the plurality of segments corresponds to a region of the at least portion of the subject's GIT;
   obtaining a set of values for each segment of the plurality of segments, wherein for each segment, the respective set of values refers to the pathological involvement of the respective segment in the mucosal disease and to severity of mucosal manifestation of the mucosal disease in the respective segment, the set of values for each segment obtained by, for each segment:
      providing a user interface screen indicating the respective segment,
      causing the user interface screen to display images from the stream of images that are part of the respective segment while the respective segment is indicated on the user interface screen,
      causing the user interface screen to display a graphical control element having a plurality of selectable values while the images that are part of the respective segment are displayed, and
      receiving at least one value of the respective set of values for the respective segment, via the graphical control element, by a user selection of one of the plurality of selectable values; and
   based on the set of values for each segment, generating, in the user interface screen, a representation indicating location and severity of the mucosal manifestation of the mucosal disease in the entirety of the at least portion of the subject's GIT;
   at least one hardware processor configured to execute said instructions; and
   a display configured to display the user interface screen and the generated representation.

18. A non-transitory processor-readable medium storing instructions which, when executed by one or more processors of a system, cause the system to:
   receive a stream of images of at least a portion of the subject's GIT;
   parse the stream of images into a plurality of segments, wherein each segment of the plurality of segments corresponds to a region of the at least portion of the subject's GIT;
   obtain a set of values for each segment of the plurality of segments, wherein for each segment, the respective set of values refers to pathological involvement of the respective segment in the mucosal disease and to severity of mucosal manifestation of the mucosal disease in the respective segment, the set of values for each segment obtained by, for each segment:
   providing a user interface screen indicating the respective segment,
   causing the user interface screen to display images from the stream of images that are part of the respective segment while the respective segment is indicated on the user interface screen,
   causing the user interface screen to display a graphical control element having a plurality of selectable values while the images that are part of the respective segment are displayed, and
   receiving at least one value of the respective set of values for the respective segment, via the graphical control element, by a user selection of one of the plurality of selectable values; and based on the set of values for each segment, generate, in the user interface screen, a representation indicating location and severity of the mucosal manifestation of the mucosal disease in the entirety of the at least portion of the subject's GIT, thereby allowing to assess the condition of the mucosal disease in the at least portion of the subject's GIT.

* * * * *